(12) United States Patent
Smithanik et al.

(10) Patent No.: US 9,538,963 B2
(45) Date of Patent: Jan. 10, 2017

(54) DIAGNOSTIC SCANNING APPARATUS

(71) Applicants: SKF Magnetic Bearings, Calgary (CA); Siemens Aktiengesellschaft, Munich (DE)

(72) Inventors: Jeffrey Russell Smithanik, Calgary (CA); Christian Willming, Forchheim (DE); Craig McFarland, Calgary (CA); Hans-Juergen Mueller, Forchheim (DE); Wray Sparling, Calgary (CA)

(73) Assignee: AKTIEBOLAGET SKF, Gothenburg (SE)

( * ) Notice: Subject to any disclaimer, the term of this patent is extended or adjusted under 35 U.S.C. 154(b) by 574 days.

(21) Appl. No.: 13/838,217

(22) Filed: Mar. 15, 2013

(65) Prior Publication Data
US 2014/0270051 A1 Sep. 18, 2014

(51) Int. Cl.
*A61B 6/00* (2006.01)
*A61B 6/03* (2006.01)
*F16C 19/50* (2006.01)
*F16C 32/04* (2006.01)

(52) U.S. Cl.
CPC ............ *A61B 6/035* (2013.01); *A61B 6/44* (2013.01); *A61B 6/4435* (2013.01); *F16C 19/507* (2013.01); *F16C 32/0485* (2013.01)

(58) Field of Classification Search
CPC ......... A61B 6/035; A61B 6/44; F16C 32/0453
See application file for complete search history.

(56) References Cited

U.S. PATENT DOCUMENTS

| 5,155,402 | A | * | 10/1992 | Bichler ................ 310/90.5 |
| 5,196,748 | A | | 3/1993 | Rigney |
| 5,268,955 | A | | 12/1993 | Burke et al. |
| 5,305,363 | A | | 4/1994 | Burke et al. |
| 5,481,585 | A | | 1/1996 | Kimura et al. |
| 5,493,599 | A | | 2/1996 | Mattson |
| 5,548,629 | A | | 8/1996 | Kimura et al. |
| 6,276,145 | B1 | | 8/2001 | Sharpless et al. |
| 6,404,845 | B1 | | 6/2002 | Sharpless et al. |
| 6,563,244 | B1 | | 5/2003 | Yamauchi et al. |

(Continued)

FOREIGN PATENT DOCUMENTS

WO 2010/026523 A2 3/2010
WO 2012/006527 A1 1/2012

*Primary Examiner* — David J Makiya
*Assistant Examiner* — Dani Fox
(74) *Attorney, Agent, or Firm* — Mark Ussai; SKF USA Inc. Patent Dept.

(57) ABSTRACT

A diagnostic scanning apparatus includes a hollow rotor sized to receive a patient. First and second flanges are connected to and extend radially outward from the rotor in a spaced-apart relationship, each of the first and second flanges including, at least in part, a magnetically-permeable material. A radiation source is affixed to the first flange and/or the rotor. A first axial actuator generates a variable magnetic field, is fixedly disposed adjacent to the first flange and can magnetically pull the first flange in a first axial direction of the rotor. A second axial actuator generates a variable magnetic field, is fixedly disposed adjacent to the second flange and can magnetically pull the second flange in a second axial direction of the rotor that is opposite of the first axial direction. The first and second axial actuators are both at least substantially disposed between the first and second flanges.

20 Claims, 13 Drawing Sheets

(56) References Cited

U.S. PATENT DOCUMENTS

| | | | |
|---|---|---|---|
| 6,748,806 B2 | 6/2004 | Halsmer | |
| 7,023,952 B2 | 4/2006 | Brunnett | |
| 7,277,523 B2 | 10/2007 | Mattson | |
| 8,270,563 B2 | 9/2012 | Harris et al. | |
| 2007/0153977 A1 | 7/2007 | Yokoyama et al. | |
| 2010/0034492 A1* | 2/2010 | Krumme | 384/107 |
| 2011/0194669 A1* | 8/2011 | Tremaine et al. | 378/15 |

\* cited by examiner

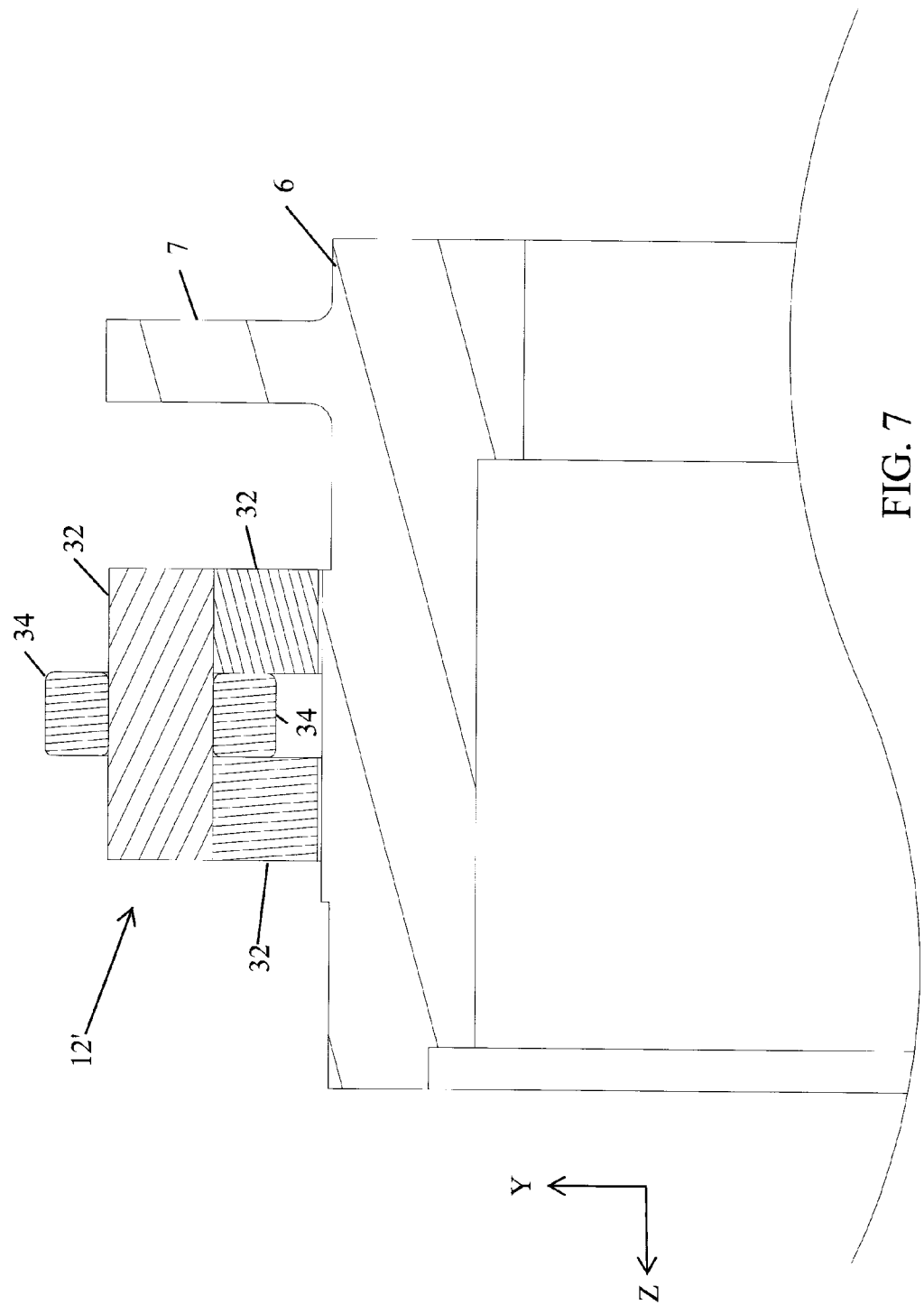

DIAGNOSTIC SCANNING APPARATUS

TECHNICAL FIELD

The present teachings generally relate to a diagnostic scanning apparatus, such as a computed tomography imaging system, having one or more magnetic bearings for rotatably supporting an annular rotor or gantry. The present teachings also relate more generally to arrangements for rotatably supporting an annular rotor, which rotates, e.g., in a substantially vertical or horizontal plane, using one or more magnetic bearings.

BACKGROUND ART

Known computed tomography (CT) imaging systems include a rotatable annular gantry or rotor having a gantry bore for receiving a patient or other object to be internally imaged. In typical CT applications, an x-ray source is mounted on the annular gantry and radiates a fan-shaped, wedge-shaped, or cone-shaped x-ray beam in the plane of gantry rotation. The x-ray beam passes through the patient while the annular gantry is rotating and the attenuated x-rays are sensed by a detector array disposed on the gantry opposite to the x-ray source.

Thus, while the annular gantry is rotating, a series of x-ray projections or 2-D slices of the patient are obtained at different angles. These projections are mathematically reconstructed to create a tomographic image of each slice. The patient may be moved axially through the bore to obtain data on adjacent slices and the slices may be combined to generate a 3-D image of interest.

Generally speaking, higher rotational speeds are desired in order to reduce the time required to obtain the tomographic image of interest and/or to provide high-speed or "freeze motion" images. However, higher rotational speeds often lead to problems with respect to the static and dynamic balance of the rotating annular gantry.

In the past, it has been attempted to maintain the balance of the gantry by setting very tight tolerances for the center of gravity and the masses of the components mounted on the gantry. These components generally include the x-ray source and detector, signal processing circuitry, power supplies and cooling systems. The gantry may then be manually balanced by adding and adjusting balancing weights, which is a time consuming and difficult task.

Thus, the need to dynamically offset any imbalances arising during operation has required relatively complex solutions, such as the solution described in U.S. Pat. No. 6,748,806, which changes the position of movable weights disposed on the annular gantry during operation to maintain the dynamic balance of the annular gantry.

Further, if it becomes necessary to replace or service the mechanical bearings supporting the gantry, subsequent field rebalancing is more difficult than balancing at the time of manufacturing and also leads to a loss of valuable usage time for the system. In addition, the re-application of lubricants, e.g., bearing grease, in a sterile environment such as a medical facility is also problematic.

U.S. Pat. No. 7,277,523 mentions the use of high speed mechanical bearings, air bearings, magnetic beatings, or the like to rotatably support the annular gantry, but provides no details concerning the construction of the bearings. U.S. Pat. No. 7,023,952 discloses air bearings for rotatably supporting the annular gantry of a diagnostic scanning device.

WO 2010/026523 A2 discloses a rotating ring apparatus that includes magnetic levitation means for levitating and rotating a rotating ring relative to a stationary ring.

U.S. Pat. No. 5,481,585 discloses a CT machine that utilizes magnetic levitation magnets to levitate a rotor, which is rotated about its rotational axis using a separate drive means.

US 2011/0194669 discloses a diagnostic scanning apparatus, such as a CT machine, that uses a magnetic bearing system and provides a significant improvement over the prior art. However, further improvements are possible.

SUMMARY

It is an object of the present disclosure to provide an improved diagnostic scanning apparatus, e.g., an improved computed tomography imaging system.

In addition or in the alternative, it is an object of the present disclosure to provide improved designs for rotatably supporting an annular rotor using a magnetic bearing system or arrangement.

In one aspect of the present teachings, a magnetic bearing arrangement for a rotor is disclosed, which uses the concept of magnetic levitation to lift and/or to rotatably support the rotor so that it can rotate in a friction-free manner. The rotor is preferably designed to rotate about a substantially horizontal axis, such that the radial direction of the rotor is in a vertical or substantially vertical plane. However, such a system can also be designed to permit tilting of the rotational axis, e.g., by +/−30° or more.

In another aspect of the present teachings, the rotor may rotate about a vertical axis or a substantially vertical axis, which again may be tiltable, e.g., by +/−30° or more.

In another aspect of the present teachings, an apparatus preferably includes a rotor that rotates about a rotational axis. A magnetic bearing system influences the position of the annular rotor in three-dimensional space and preferably may include at least three actuators, such as at least one actuator that generates a force for lifting the annular rotor in a vertical direction, at least one actuator that influences the position of the annular rotor in the radial direction of the rotor and at least assists in maintaining an annular gap between at least one non-magnetic bearing and the annular rotor in the radial direction during operation and at least one actuator that influences the position of the annular rotor in an axial direction of the rotor. The lift actuator may be combined with one of the radial actuator and/or the axial actuator, such that, e.g., the radial actuator also performs a rotor-lifting function and/or the axial actuator also performs a rotor-lifting function.

Such an apparatus may further comprise at least one radiation source mounted on the rotor such that the apparatus is configured for scanning and/or imaging applications.

In addition or in the alternative, the apparatus preferably includes first and second flanges that are connected to and extend radially outward from the rotor in a spaced-apart relationship and define a well or hollow space therebetween, i.e. the rotor body and the first and second flanges preferably form a U-shape in axial cross-section that defines the well or hollow space. At least the actuator that influences the position of the annular rotor in the axial direction of the rotor is fixedly disposed within the well or hollow space, although preferably all actuators are disposed within the well or hollow space.

In addition or in the alternative, the apparatus may preferably include a stationary housing or frame having a mounting flange (or stator) extending radially inward into the well or space defined by the first and second flanges. One or more pieces of equipment may be affixed to the mounting flange, such as one or more of the above-mentioned actuators designed to actively adjust or control the position of the annular rotor during operation, one or more permanent magnets designed to passively lift the annular rotor, one or more permanent magnets designed to offset a tilting force or moment caused by the weight of any equipment (such as the radiation source and/or detector) attached to the rotor and/or one of the flanges, one or more axial landing pads for protecting the equipment affixed to the mounting flange and/or for axially supporting the rotor in the event of a malfunction, such as a loss of power.

In addition or in the alternative, the one or more permanent magnets designed to offset the tilting force or moment caused by the weight of any equipment (such as the radiation source and/or detector) attached to the rotor and/or a flange thereof may be used with a rotor having no flange, a single radially-extending flange or at least two radially-extending flanges. In an embodiment that utilizes no flange or a single radially-extending flange, preferably at least one first permanent magnet is disposed on one axial side of the rotor and/or the single radially-extending flange and at least one second permanent magnet is disposed on the opposite axial side of the rotor and/or the single radially-extending flange. The first and second permanent magnets may be, e.g., respectively affixed to two mounting flanges that radially-inwardly extend from the stationary housing. The at least one first permanent magnetic is preferably disposed higher in the vertical direction of the stationary housing or the rotor than the at least one second permanent magnet. Further, the at least one first permanent magnet is preferably disposed on the axial side of the rotor and/or the single-radially extending flange that is axially opposite of the equipment (e.g., a radiation source and/or detector), which is attached to the rotor and causes the tilting force or moment. The lower-disposed, at least one second permanent magnet is preferably disposed on the same axial side of the rotor and/or the single-radially extending flange as the tilt-causing equipment.

In addition or in the alternative, the one or more axial landing pads for protecting the equipment affixed to the mounting flange and/or for axially supporting the rotor in the event of a malfunction, such as a loss of power, may be used with a rotor having no flange, a single radially-extending flange or at least two radially-extending flanges. In an embodiment that utilizes no flange or a single radially-extending flange, preferably at least one first axial landing pad is disposed on one axial side of the rotor and/or the single radially-extending flange and at least one second axial landing pad is disposed on the opposite axial side of the rotor and/or the single radially-extending flange. The first and second axial landing pads may be, e.g., respectively affixed to two mounting flanges that radially-inwardly extend from the stationary housing. The first and second axial landing pads may optionally be disposed in pairs around the circumference of the rotor (or a flange thereof) or may be disposed offset from each other in the circumferential direction.

In further aspects of the present teachings, the following, non-limiting embodiments are disclosed:

1. An apparatus comprising:
a rotor (e.g., an annular rotor) that is rotatable about a rotational axis, has a hollow interior and comprises, at least in part, a magnetically-permeable material,
first and second flanges connected to and extending radially outward from the rotor in a spaced-apart relationship, each of the first and second flanges comprising, at least in part, a magnetically-permeable material,
a first axial actuator configured to generate a variable magnetic field and being fixedly disposed adjacent to the first flange, the first axial actuator being configured to magnetically pull the first flange (and thus the rotor) in a first axial direction of the rotor, and
a second axial actuator configured to generate a variable magnetic field and being fixedly disposed adjacent to the second flange, the second axial actuator being configured to magnetically pull the second flange (and thus the rotor) in a second axial direction of the rotor that is opposite of the first axial direction,
wherein the first and second axial actuators are both disposed between the first and second flanges.

2. The apparatus as in embodiment 1, wherein the first flange is formed integrally with the rotor without a seam therebetween and the second flange is detachably attached to the rotor.

3. The apparatus as in embodiment 1 or 2, wherein:
the first and second flanges are annular shaped,
the first and second annular flanges extend at least substantially in parallel to each other, and
the rotor and the first and second annular flanges form a rotor assembly having at least substantially a U-shape in cross-section.

4. The apparatus as in embodiment 3, wherein a well or hollow space is defined by adjacent surfaces of the rotor and the first and second annular flanges.

5. The apparatus as in any one of embodiments 1-4, wherein the first and second axial actuators each comprise at least one coil wound around at least one stator core.

6. The apparatus as in any one of embodiments 1-5, wherein:
the first and second axial actuators each comprise a substantially U-shaped stator core defining first and second legs and
first and second coils are respectively wound around the first and second legs of the stator core.

7. The apparatus as in any one of embodiments 1-6, further comprising:
a stationary housing having a mounting flange, e.g., an annular mounting flange, extending radially inward from the stationary housing into a (the) well or hollow space between the first and second (annular) flanges,
wherein the first axial actuator is affixed to a first axial side of the (annular) mounting flange that is closest to the first (annular) flange, and
the second axial actuator is affixed to a second axial side of the (annular) mounting flange that is closest to the second (annular) flange, the second axial side being opposite of the first axial side.

8. The apparatus as in embodiment 7, where in the apparatus comprises:
at least three first axial actuators affixed to the first axial side of the (annular) mounting flange and being spaced, preferably approximately equidistantly to each other, around the circumference of the (annular) mounting flange; and
at least three second axial actuators affixed to the second axial side of the (annular) mounting flange and being spaced, preferably approximately equidistantly, to each other around the circumference of the (annular) mounting flange.

9. The apparatus as in any one of embodiments 7 or 8, further comprising:
at least one bracket affixed to the rotor and/or to first (annular) flange and extending axially outward of the rotor and the first (annular) flange, at least one first permanent magnet affixed to the first axial side of the (annular) mounting flange, and at least one second permanent magnet affixed to the second axial side of the (annular) mounting flange.

10. The apparatus as in embodiment 9, wherein the at least one bracket is attached to a radiation source or to a radiation detector.

11. The apparatus as in embodiment 9 or 10, wherein the at least one first permanent magnet and the at least one second permanent magnet together apply no net force to the rotor in the axial direction, but apply a net torque or moment to the rotor that balances or offsets a tilting force (load) or moment generated by the weight of the bracket and any equipment attached to the bracket, such as the radiation source or the radiation detector, which is disposed axially outward of the rotor and first (annular) flange.

12. The apparatus as in any one of embodiments 9-11, wherein the at least one first permanent magnet is disposed higher in the vertical direction of the stationary housing than the at least one second permanent magnet.

13. The apparatus as in any one of embodiments 9-12, wherein the at least one first permanent magnet is disposed generally at or proximal to an uppermost vertical position of the (annular) mounting flange and the at least one second permanent magnet is disposed generally at or proximal to a lowermost vertical position of the (annular) mounting flange.

14. The apparatus as in any one of embodiments 9-13, wherein the at least one first permanent magnet and/or the at least one second permanent magnet is comprised of at least two separate and distinct permanent magnets that are spaced apart in a mirror-symmetric manner relative to a vertical axis of the rotor that extends through the rotational axis of the rotor.

15. The apparatus as in any one of embodiments 9-14, further comprising a steel channeling plate or member affixed to each permanent magnet.

16. The apparatus as in any one of embodiments 9-15, further comprising:

at least one first landing pad affixed to the first axial side of the (annular) mounting flange so as to be proximal to the first (annular) flange, and at least one second landing pad affixed to the second axial side of the (annular) mounting flange so as to be proximal to the second (annular) flange.

17. The apparatus as in embodiment 16, wherein the at least one first landing pad and/or the at least one second landing pad is a plain bearing or plain bearing pad.

18. The apparatus as in embodiment 16 or 17, wherein the at least one first landing pad and/or the at least one second landing pad comprises an abradable material, such as an abradable graphite material.

19. The apparatus as in any one of embodiments 16-18, wherein the at least one first landing pad and/or the at least one second landing pad have an outer axial surface that is spaced farther from the (annular) mounting flange than any other equipment affixed to the (annular) mounting flange.

20. The apparatus as in any one of embodiments 16-19, further comprising two or more first landing pads and/or two or more second landing pads, each being disposed preferably equidistantly around the circumference of the (annular) mounting flange.

21. An apparatus, comprising:

a rotor, which optionally has no flange, a single first flange radially extending outward from the rotor, or at least first and second (e.g., annular) flanges connected to and extending radially outward from the rotor in a spaced-apart relationship, each of the rotor and the optional first and/or second (annular) flanges comprising, at least in part, a magnetically-permeable material, the rotor being rotatable about a rotational axis, at least one bracket or drum affixed to the rotor or the optional first (annular) flange and extending axially outward of the rotor and the optional first (annular) flange in a first axial direction, at least one first permanent magnet configured to magnetically pull the rotor and/or the optional flange(s) in the first axial direction, and at least one second permanent magnet configured to magnetically pull the rotor and/or the optional flange(s) in a second axial direction, the second axial direction being (linearly) opposite of the first axial direction.

22. The apparatus as in embodiment 21, wherein the at least one bracket is attached to at least one piece of equipment to be rotated by the rotor, such as a radiation source and/or a radiation detector.

23. The apparatus as in embodiment 21 or 22, wherein the drum contains at least one piece of equipment to be rotated by the rotor, such as a radiation source and/or a radiation detector, the drum optionally being affixed to the rotor and/or the optional flange(s) via at least one bracket.

24. The apparatus as in any one of embodiments 21-23, wherein the at least one first permanent magnet and the at least one second permanent magnet together apply no net force to the rotor in the axial direction, but apply a net torque or moment to the rotor that balances or offsets a tilting force (load) or moment generated by the weight of the bracket and the equipment attached thereto, e.g., the radiation source and/or the radiation detector.

25. The apparatus as in any one of embodiments 21-24, wherein the at least one first permanent magnet is disposed lower in the vertical direction of the rotor than the at least one second permanent magnet.

26. The apparatus as in any one of embodiments 21-25, wherein the at least one second permanent magnet is disposed generally at or proximal to an uppermost vertical position of the rotor or the optional (annular) flange(s) and the at least one first permanent magnet is disposed generally at or proximal to a lowermost vertical position of the rotor or the optional (annular) flange(s).

27. The apparatus as in any one of embodiments 21-26, wherein the at least one first permanent magnet and/or the at least one second permanent magnet is comprised of at least two separate and distinct permanent magnets that are spaced apart in a mirror-symmetric manner relative to a vertical axis of the rotor that extends through the rotational axis of the rotor.

28. The apparatus as in any one of embodiments 21-27, further comprising a steel channeling plate or member affixed to each permanent magnet.

29. The apparatus as in any one of embodiments 21-28, further comprising:

a stationary housing having at least one (e.g., annular) mounting flange extending radially inward from the stationary housing, e.g., one of: (i) so as to be adjacent to a radially-extending face of the rotor, (ii) so as to be adjacent to a radially-extending face of the optional single (annular) flange or (iii) into a space between the optional first and second (annular) flanges, wherein the at least one first permanent magnet is affixed on a first axial side of the at least one (annular) mounting flange, and the at least one second permanent magnet is affixed on a second axial side of the at least one (annular) mounting flange, the second axial side being opposite of the first axial side.

30. The apparatus as in any one of embodiments 21-29, further comprising:
at least one first landing pad affixed proximal to a first axial side of the rotor or the optional (annular) flange(s), and
at least one second landing pad affixed proximal to a second axial side of the rotor or the optional (annular) mounting flange(s).

31. The apparatus as in embodiment 30, wherein the at least one first landing pad and/or the at least one second landing pad is a plain bearing or plain bearing pad.

32. The apparatus as in embodiment 30 or 31, wherein the at least one first landing pad and/or the at least one second landing pad comprises an abradable material, such as an abradable graphite material.

33. The apparatus as in any one of embodiments 30-32, wherein the at least one first landing pad and/or the at least one second landing pad have a width in the axial direction that is wider than the axial width of any equipment, such as an axial actuator, affixed axially adjacent to the rotor and/or the optional (annular) flange(s).

34. The apparatus as in embodiment 33, wherein the at least one first landing pad and/or the at least one second landing pad have an outer axial surface that is spaced farther from the at least one (annular) mounting flange than any other equipment affixed to the at least one (annular) mounting flange.

35. The apparatus as in any one of embodiments 30-34, further comprising two or more first landing pads and/or two or more second landing pads, each being disposed preferably equidistantly around the circumference of the at least one (annular) mounting flange.

36. An apparatus, comprising:
an rotor, which optionally has no flange, a single first flange radially extending outward from the rotor, or at least first and second (e.g., annular) flanges connected to and extending radially outward from the rotor in a spaced-apart relationship, each of the rotor and the optional first and/or second (annular) flanges comprising, at least in part, a magnetically-permeable material, the rotor being rotatable about a rotational axis,
at least one first landing pad affixed proximal to a first axial side of the rotor and/or the (annular) flange(s), and
at least one second landing pad affixed proximal to a second axial side of the rotor and/or the (annular) flange(s), the second axial side being opposite of the first axial side.

37. The apparatus as in embodiment 36, wherein the at least one first landing pad and/or the at least one second landing pad is a plain bearing or plain bearing pad.

38. The apparatus as in embodiment 36 or 37, wherein the at least one first landing pad and/or the at least one second landing pad comprises an abradable material, such as an abradable graphite material.

39. The apparatus as in any one of embodiments 36-38, further comprising:
a stationary housing having at least one (e.g., annular) mounting flange extending radially inward from the stationary housing, e.g., one of: (i) so as to be adjacent to a radially-extending face of the rotor, (ii) so as to be adjacent to a radially-extending face of the optional single (annular) flange or (iii) into a space between the optional first and second (annular) flanges,
wherein the at least one first landing pad is affixed on a first axial side of the at least one (annular) mounting flange, and
the at least one second landing pad is affixed on a second axial side of the at least one (annular) mounting flange, the second axial side being opposite of the first axial side.

40. The apparatus as in any one embodiments 36-39, wherein the at least one first landing pad and/or the at least one second landing pad have a width in the axial direction that is wider than the axial width of any equipment, such as an axial actuator, affixed axially adjacent to the rotor and/or the optional (annular) flange(s).

41. The apparatus as in embodiment 40, wherein the at least one first landing pad and/or the at least one second landing pad have an outer axial surface that is spaced farther from the at least one (annular) mounting flange than any other equipment affixed to the (annular) mounting flange.

42. The apparatus as in any one of embodiments 36-41, further comprising two or more first landing pads and/or two or more second landing pads, each being disposed preferably equidistantly around the circumference of the (annular) mounting flange.

43. The apparatus as in any one of embodiments 1-42, wherein the rotational axis of the rotor extends substantially in a horizontal direction and is optionally tiltable by +/−30°.

44. The apparatus as in any one of embodiments 1-43, further comprising:
at least one lift actuator configured to generate a force that lifts the rotor in a (the) vertical direction and is disposed between the first and second (annular) flanges.

45. The apparatus as in embodiment 44, wherein the at least one lift actuator comprises at least one permanent magnet configured to lift at least 50%, more preferably at least 70%, more preferably at least 80% and even more preferably at least 95%, of the weight of the rotor, the first and second flanges and any further equipment attached thereto.

46. The apparatus as in embodiment 44 or 45, wherein the at least one lift actuator comprises an electromagnet configured to generate a variable magnetic field.

47. An apparatus as in any one of embodiments 44-46, wherein the at least one lift actuator comprises at least one of a passive homopolar actuator, an active homopolar actuator, a passive heteropolar actuator and/or an active heteropolar actuator.

48. The apparatus as in any one of embodiments 1-47, further comprising:
at least one radial actuator configured to influence the position of the rotor in the radial direction of the rotor and to at least assist in maintaining an (annular) gap between the rotor and at least one non-magnetic bearing in the radial direction of the rotor while the rotor is rotating, the at least one radial actuator being attached to the (annular) mounting flange of the stationary housing and disposed between the first and second flanges of the rotor.

49. The apparatus as in embodiment 48, wherein the apparatus comprises at least first and second pairs of radial actuators disposed around the outer circumference of the rotor and attached to the (annular) mounting flange of the stationary housing, optionally such that the two radial actuators in each of the first and second pairs of radial actuators are equally spaced from a (the) vertical axis in a mirror-symmetric manner, e.g., by 45° from the vertical axis.

50. An apparatus as in embodiment 48 or 49, wherein the radial and/or axial actuators each comprise an active heteropolar actuator and/or an active homopolar actuator.

51. The apparatus as in any one of embodiments 1-50, further comprising:

at least one non-magnetic bearing disposed adjacent to and radially outward of the rotor, the at least one non-magnetic bearing being capable of rotatably supporting the rotor at least temporarily, wherein the outer circumference of the rotor preferably has a diameter slightly less than the diameter of a radially-inward-facing surface of the non-magnetic bearing.

52. The apparatus as in embodiment 51, wherein the at least one non-magnetic bearing is selected from a plain bearing and a rolling-element bearing.

53. The apparatus as in any one of embodiments 1-52, wherein the rotor has an outer diameter that is greater than its longitudinal length.

54. The apparatus as in any one of embodiments 1-53, wherein the rotor has a hollow interior sized to receive a patient therein.

55. The apparatus as in any one of embodiments 1-54, wherein the apparatus is a diagnostic scanning apparatus and further comprises a (the) radiation source mounted on the rotor, e.g., via a (the) bracket, so as to rotate therewith.

56. The apparatus as in any one of embodiments 1-55, wherein the rotor comprises a laminated magnetically-permeable material, (the) radial actuator(s) comprise(s) a heteropolar actuator, the radial actuator(s) comprise(s) laminations that extend parallel to the magnetic flux path and/or the axial actuators are homopolar.

57. The apparatus as in any one of embodiments 1-56, wherein the rotor has an outer diameter that is greater than its longitudinal length, the rotor outer diameter preferably being at least 2 times greater than the longitudinal length, more preferably at least 5 times greater than the longitudinal length, even more preferably at least 8 times greater than the longitudinal length and still more preferably at least 10 times greater than the longitudinal length.

58. The apparatus as in any one of embodiments 1-57, wherein (the) at least one radial actuator is replaced with a non-magnetic bearing configured to rotatably support the rotor in the radial direction of the rotor, the non-magnetic bearing optionally being, e.g., a plain bearing or a roller-element bearing.

59. The apparatus as in any one of embodiments 1-58, wherein (the) at least one axial actuator is replaced with a non-magnetic bearing configured to guide the rotor in the axial direction of the rotor, the non-magnetic bearing optionally being, e.g., a plain bearing or a roller-element bearing.

60. The apparatus as in any one of embodiments 1-59, further comprising at least one position sensor configured to detect the position of the rotor in the radial and/or axial directions.

61. The apparatus as in any one of embodiments 1-60, further comprising at least one auxiliary, non-magnetic bearing mounted on the stationary housing and being configured to support the annular rotor, e.g., at least when the annular rotor is not rotating, and/or to rotatably support the annular rotor at least temporarily, e.g., during a fault or malfunction in the magnetic bearing system.

62. A method of scanning, imaging or treating a patient or an object comprising:

rotating the rotor of the apparatus of any one of embodiments 1-61 and actuating a (the) rotating radiation source attached to the rotor to irradiate the patient or the object.

63. A method as in embodiment 62, further comprising detecting attenuated radiation signals after passing through or being scattered by the patient or the object being scanned or imaged.

Certain advantages may result due to the construction and/or arrangement of one or more of the above-identified embodiments or of other embodiments disclosed herein, including but not limited to:

(i) improved reliability and/or reduced maintenance, which provides more operational time for the machine, thereby improving productivity, (ii) reduced noise and/or vibration, which may make the machine less intimidating for an operator or patient, and which may also serve to further improve reliability and service life, (iii) greater tolerance of unbalance in the rotor system due to the capability of the magnetic bearing system to compensate for unbalance during operation by adjusting magnetic forces generated by one or more of the actuators, which may reduce the necessary manufacturing tolerances for balancing purposes and thus also may reduce manufacturing costs and/or service costs for re-balancing, (iv) avoiding or reducing problems inherent to roller bearings, which require a defined clearance-play with narrow manufacturing tolerance, (v) automatic adjustment of the gantry/rotor location in three-dimensional space in real-time through electronic control, rather than through mechanical adjustments to the rotor/gantry and/or the mechanical bearings supporting the gantry/rotor, which must be made when the system is not operating, (vi) reduced or no lubrication requirements, thereby minimizing or eliminating the amount of grease that must be used, e.g., in a sterile environment, such as a hospital or other medical facility, (vii) increased rotational speeds, which may help to reduce the time necessary to collect the necessary scanning images and thereby reduce the patient's or object's exposure to the radiation source and/or may help to obtain high speed images in order to freeze motion (i.e. generate images with little or no motion blur), such as when scanning a beating heart, and/or (viii) reduced or no wear on the primary rotating components of the system due to the lack of physical contact, e.g., between the rotor and the supporting bearings, thereby further reducing maintenance requirements and extending service life of the system, (ix) reduced or no sensitivity to contaminants in the surrounding environment, (x) on-line/remote monitoring of system conditions is possible due to the electronic control of the magnetic bearing components, (xi) low torque loss during operation, (xii) less sensitivity to impacts due to automatic position adjustment/correction by the magnetic bearing components, and/or (xiii) less strict manufacturing tolerances, e.g., for the rotor and attached components.

It is understood that the claims of the patent as granted may provide none, one or more of the above-identified or below-described advantages and/or may provide one or more advantages not explicitly mentioned herein.

Further embodiments, advantages, features and details of the present teachings are derivable from the following description of the exemplary embodiments in view of the Figures.

BRIEF DESCRIPTION OF THE DRAWINGS

FIG. 7 shows a detailed cross-sectional view of a radial actuator shown in FIG. 5.

DETAILED DESCRIPTION OF THE INVENTION

Each of the additional features and teachings disclosed below may be utilized separately or in conjunction with other features and teachings to provide improved bearings for annular rotors and/or bearing assemblies and/or diagnostic scanning systems, as well as methods for designing, constructing and using the same. Representative examples of the present invention, which examples utilize many of these additional features and teachings both separately and in combination, will now be described in further detail with reference to the attached drawings. This detailed description is merely intended to teach a person of skill in the art further details for practicing preferred aspects of the present teachings and is not intended to limit the scope of the invention. Therefore, combinations of features and steps disclosed in the following detailed description may not be necessary to practice the invention in the broadest sense, and are instead taught merely to particularly describe representative examples of the present teachings.

Moreover, the various features of the above Summary section, the representative examples and the dependent claims may be combined in ways that are not specifically and explicitly enumerated in order to provide additional useful embodiments of the present teachings. In addition, it is expressly noted that all features disclosed in the description and/or the claims are intended to be disclosed separately and independently from each other for the purpose of original disclosure, as well as for the purpose of restricting the claimed subject matter independent of the compositions of the features in the embodiments and/or the claims. It is also expressly noted that all value ranges or indications of groups of entities disclose every possible intermediate value or intermediate entity for the purpose of original disclosure, as well as for the purpose of restricting the claimed subject matter.

Figure 1:
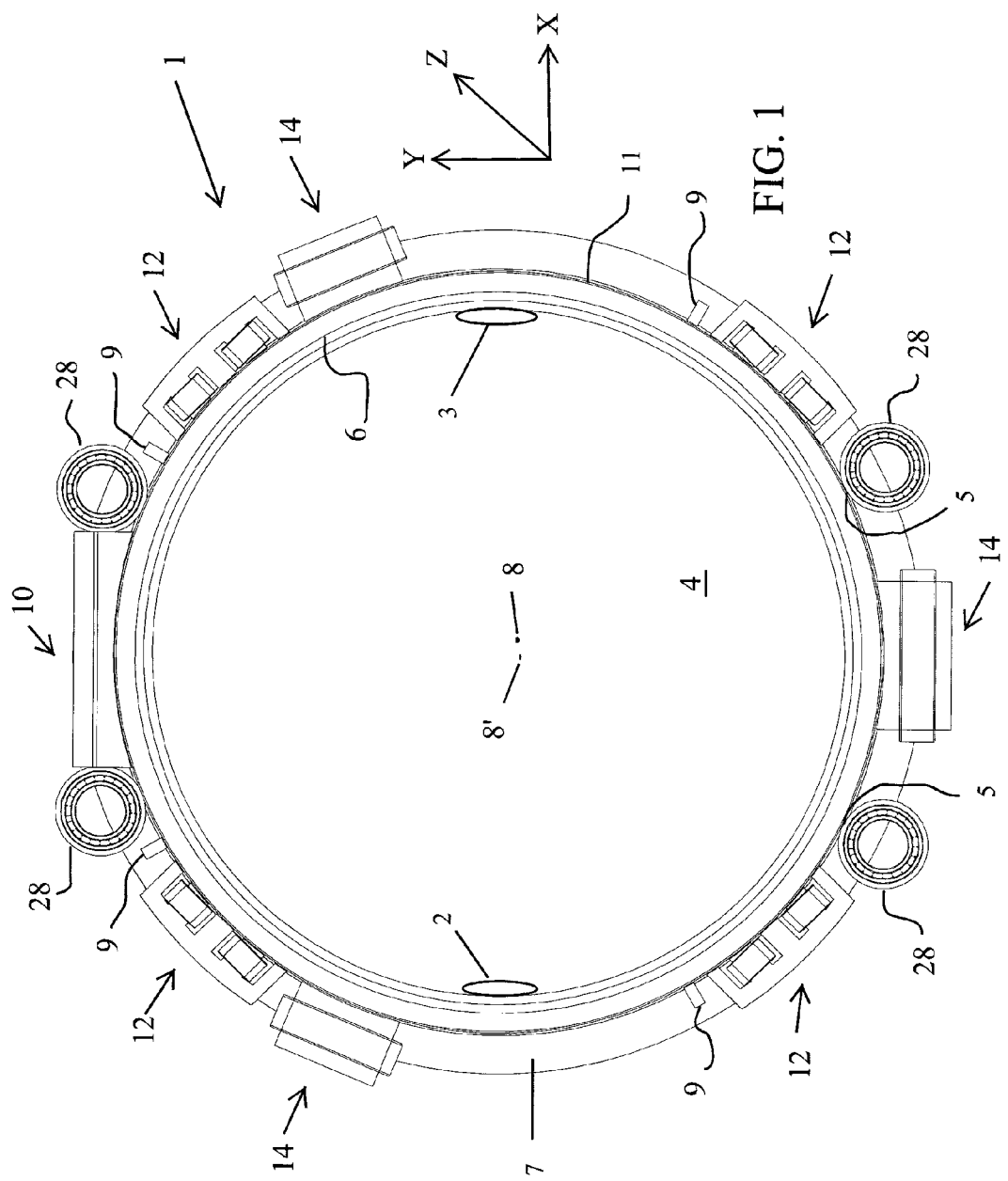
FIG. 1 shows an elevation view of a first representative embodiment of the present teachings.

FIG. 1 shows a side view of a first representative bearing arrangement for a ring-shaped rotor, which may be used, e.g., in a computed tomography (CT) machine 1. As indicated by the directional arrows on the right side of the drawing, the sheet of the drawing represents an X-Y plane and a Z-axis extends perpendicular to the sheet of the drawing, i.e. perpendicular to the X-Y plane.

Generally speaking, the computed tomography machine 1 may include a stationary gantry housing (not shown) having a central bore extending along the Z-axis. A patient table may be inserted into the bore and moved along the Z-axis in order to scan a patient or other object lying on the table. The bore preferably has a diameter of at least one meter in preferred CT applications. However, the diameter of the bore depends upon the particular application of the present teachings and various bore diameters may be utilized. Also, as discussed below, the magnetic bearing arrangements disclosed herein are not limited to diagnostic scanning apparatus and may be used in other rotor applications. The CT machine 1 is simply a suitable embodiment for describing particular aspects of the present teachings in further detail.

A rotor or annular gantry 6 is rotatably disposed within the stationary gantry housing. The rotor 6 preferably has a substantially tubular shape in three-dimensional view, i.e. it has a hollow interior 4. The hollow interior 4 is concentric with the bore of the gantry housing, such that a patient or other object to be scanned can be placed within the hollow interior 4 of the rotor 6 during the imaging operation.

The radial direction of the rotor 6 is disposed substantially in the vertical, X-Y plane, which is the imaging plane, and the axial direction of the rotor 6 extends in the Z-direction. During operation, the rotor 6 rotates about a rotational axis 8 that extends in the horizontal or Z-direction, such that the rotor 6 rotates within the plane X-Y, i.e. the radial direction of the rotor 6 falls within a substantially vertical plane. However, the rotational plane of the rotor 6 is preferably tiltable from the vertical plane, such that the rotor 6 may rotate in a plane that preferably deviates from the vertical plane by up to about +/−30°, although greater degrees of tilt are also contemplated by the present teachings.

As will be further discussed below, an annular gap or clearance 5 exists between one or more non-magnetic or auxiliary bearing(s) 28 and the rotor 6 when the rotor 6 is rotating under the influence or guidance of the magnetic bearing system, so that a friction-free bearing of the rotor 6 is possible.

The rotor 6 has an outer circumference 11 with a diameter that is preferably slightly less than an inner diameter of the non-magnetic bearing(s) 28 disposed around the rotor 6, such that an annular gap 5 in the range of about 0.25-1.5 millimeters exists during operation and thus the overall magnetic gap is about 0.5-3.0 millimeters. However, it is preferred that the annular gap 5 is as small as possible during rotation of the rotor 6 and smaller annular gaps 5 are understood to fall within the present teachings. The size of the annular gap 5 is determined, in principle, by the manufacturing tolerances of the rotor 6, and is sized just big enough so that the rotor 6 preferably or normally does not contact any stationary part of the housing or bearing(s) 28 during normal operation (rotation).

In one embodiment, a motor may rotatably drive the rotor 6, e.g., via a gear system or a belt looped around the rotor 6. In other embodiments, the rotor 6 may be rotatably driven by a direct-drive motor, wherein the rotor of the direct-drive motor has the same or substantially the same size/diameter as the rotor 6 of the CT machine 1 and the motor rotor is directly coupled or connected to the rotor 6 of the CT machine 1.

In preferred CT applications of the present teachings, the rotor 6 supports one or more components necessary to generate the computed tomography images. For example, one or more of the following devices may be mounted on the rotor 6 so as to rotate therewith: an x-ray tube (more generally, radiation source 2) and its collimation mechanism, an x-ray detector (more generally, radiation detector 3), a data acquisition system, power supplies and cooling systems, which are well known in the art and need not be described in detail herein. Generally speaking, the components are located on the rotor 6 so that their mass and centers of gravity are substantially statically and dynamically balanced when the rotor 6 is rotating at its normal rotational speed. Precise dynamic and static balancing is normally not obtainable at desired levels of manufacturing tolerances both in the components and their placement on the rotor 6. In one optional aspect of the present teachings, dynamic imbalances may be correctable in real-time during operation by adjusting the magnetic fields of one or more types of actuators 10, 12, 14 disposed around the rotor 6.

A radiation source 2 may be mounted on the rotor 6 of FIG. 1 so that the radiation source 2 rotates together with the rotor 6. A radiation detector or detector array 3, which is configured to sense or detect attenuated radiation after it has passed through an object (e.g., a patient) located in the hollow interior 4, may be mounted on an opposite side of the rotor 6. In the alternative, a stationary detector array may be mounted on or around the stationary gantry housing, so that the detector array does not rotate with the rotor 6. As indicated above, various other types of components will ordinarily be mounted on the rotor 6, but the details of such other types of components are not particularly pertinent to the present teachings.

The various components mounted on the rotating rotor 6 may communicate with a stationary CT controller (not shown), e.g., via one or more slip rings that enable the interchange of data and power. In addition or in the alternative, communications may take place wirelessly between the components mounted on the rotor 6 and the CT controller. The CT controller optionally may also control the motor and/or the magnetic bearings (i.e. at least radial and axial actuators 12, 14), or a separate magnetic bearing controller may be provided. The CT controller processes signals from the imaging components and generates CT images for the user in a manner well known in the art.

In the first representative embodiment, which will be described now in more detail with reference to FIGS. 1-4, the rotor 6 is rotatably and axially guided by three types of magnetic bearings that will be referred to herein as actuators. Because magnetic bearings provide non-contacting rotation, they minimize maintenance and eliminate the need for lubricants.

More specifically, at least one lift actuator 10, at least one radial actuator 12 and at least one axial actuator 14 are mounted on the gantry housing (or another component attached to the gantry housing) at fixed locations relative to the rotatable rotor 6. As will be understood, the actuators 10, 12, 14 are capable of generating magnetic fields that influence the position of rotor 6 in the three-dimensional space (X, Y and Z directions). Thus, the rotor 6 comprises, at least in part, a magnetically-permeable material (i.e. a material attracted to a magnetic field), such as, but not-limited to, a ferrous material. At least the radial and axial actuators 12, 14 are preferably capable of producing a variable magnetic field, but the lift actuator 10 also may be optionally configured to produce a variable magnetic field, as will be discussed in the second representative embodiment below.

Figure 2:
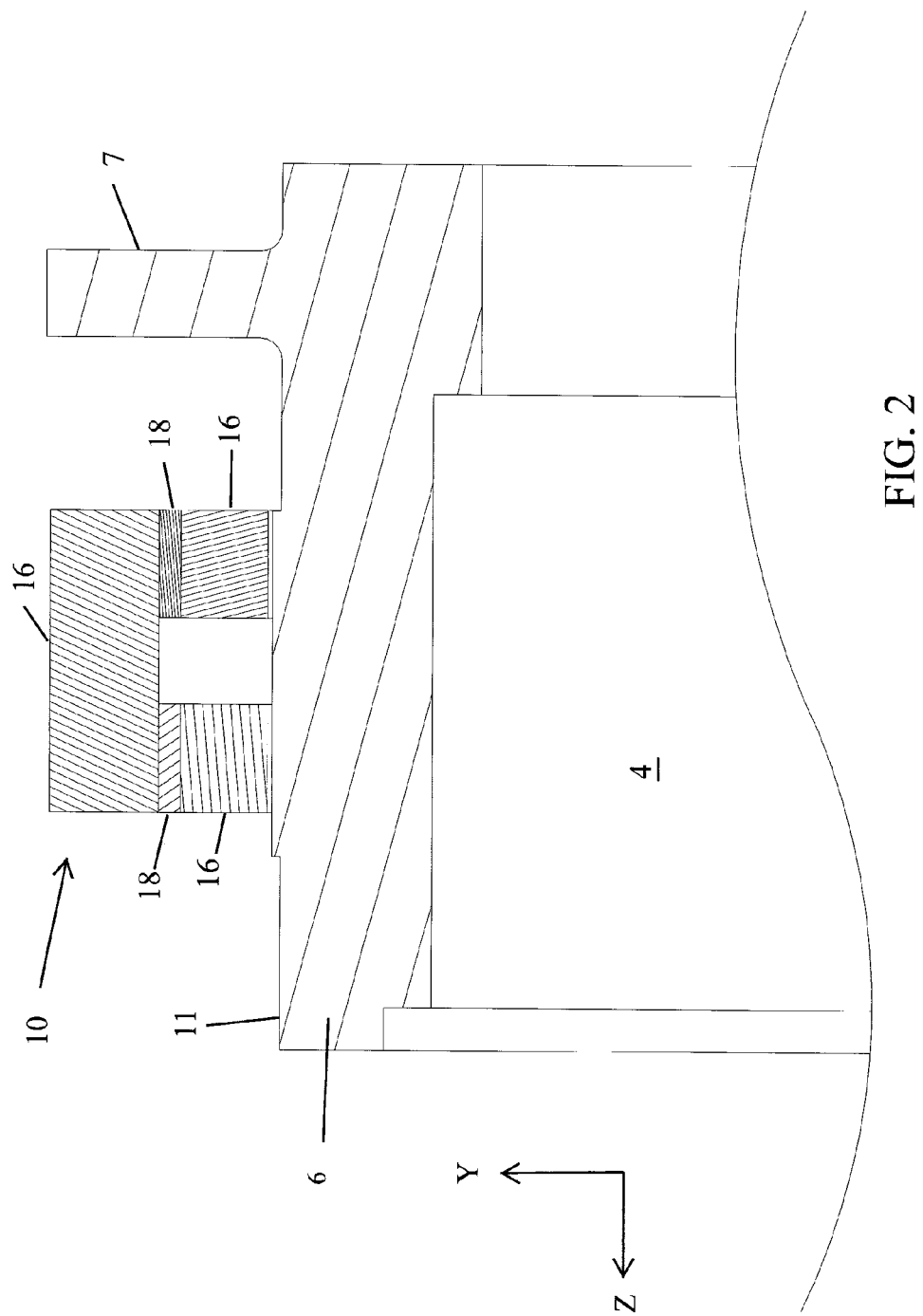
FIG. 2 shows a detailed cross-sectional view of a lift actuator shown in FIG. 1.

The at least one lift actuator 10 is preferably disposed at or adjacent to a vertically uppermost portion of the rotor 6, e.g., at the top of the X-Y plane. Referring to FIG. 2, the lift actuator 10 preferably comprises a stator core 16 and at least one permanent magnetic 18. Although the lift actuator 10 is given a reference number different from the radial actuators 12 in the present embodiment, it is understood that the lift actuator 10 may be simply a modified version of the radial actuator 12 and/or the lift actuator 10 may be replaced by a radial actuator 12 in certain embodiments, as will be further discussed below.

In CT applications of the present teachings, the weight of the rotor 6 with all the components mounted thereon may be relatively high, e.g., about 1000 kilograms. Thus, in such applications, it is cost-effective to utilize at least one permanent magnet 18 to perform the bulk or majority of the rotor-lifting work during operation for maintaining the annular gap 5 between the rotor 6 and the auxiliary bearing(s) 28. Thus, the permanent magnet 18 may be utilized to increase the overall system efficiency by reducing the load requirement on the electromagnet portions of the actuators 10 and 12 that influence the position of the rotor 6 in the radial direction thereof, i.e. in the X-Y plane.

For example, the permanent magnet 18 may be sized and selected, in a particularly preferred embodiment, such that it is capable of lifting at least about 90% of the weight of the rotor 6. More generally, the permanent magnet 18 may be sized and selected such that it is capable of lifting between about 50-150% of the weight of the rotor 6, more preferably between about 70-130%, even more preferably between about 80-120%. If the lift actuator 10 is capable of lifting 100% or more of the weight of the rotor 6, then the radial actuator(s) 12 operate, in part, to pull the rotor 6 away from the lift actuator 10 during operation, so as to maintain the annular gap 5 between the rotor 6 and the non-magnetic bearing(s) 28 disposed adjacent to the lift actuator 10. In addition or in the alternative, the lift actuator 10 may include an electromagnet configured to generate a variable magnetic field that cancels or offsets a portion of the magnetic flux generated by the permanent magnet 18, thereby giving the lift actuator 10 an overall lesser lifting capacity during operation.

Although not shown in FIG. 2, the magnetic flux path of the lift actuator 10 is a closed path, e.g., a substantially circular path, that extends generally in the Y-Z plane and goes through the various portions of the stator core 16, through the permanent magnets 18, across a clearance or gap between the rotor 6 and the stator core 16 and through the adjacent portion of the rotor 6.

As will be understood, the lift actuator 10 need not contain a permanent magnet and the entire rotor-lifting work may be performed by one or more electromagnets, for example, an electromagnet according to one of the radial actuators 12 discussed below. Further, in certain embodiments, the lift actuator 10 can be completely omitted and replaced by two or more radial actuators 12, each of which may or may not comprise a permanent magnet.

In the alternative, the lift actuator 10 may be both passive and active, i.e. it may include at least one permanent magnet and at least one coil so that it is also an electromagnet, as will be discussed below with respect to the embodiment of FIG. 6.

As with all of the directional actuators 10, 12, 14, the functionality of the actuators can be divided so that some actuators are only permanent magnets (i.e. no coil) and some actuators are only electromagnets (e.g., only a coil/stator core arrangement). For example, a single actuator disclosed herein as having both a permanent magnet and an electromagnet may be separated into two separate actuators to perform the respective passive and active magnetic functions.

Referring back to FIG. 1, four radial actuators 12 may be mounted on the gantry housing and are disposed around the circumference of the rotor 6. As will be discussed further below, the number of radial actuators 12 is variable according to the present teachings and may be more or less than four. However, generally speaking, between two to five radial actuators 12 are particularly preferred.

Figure 3:
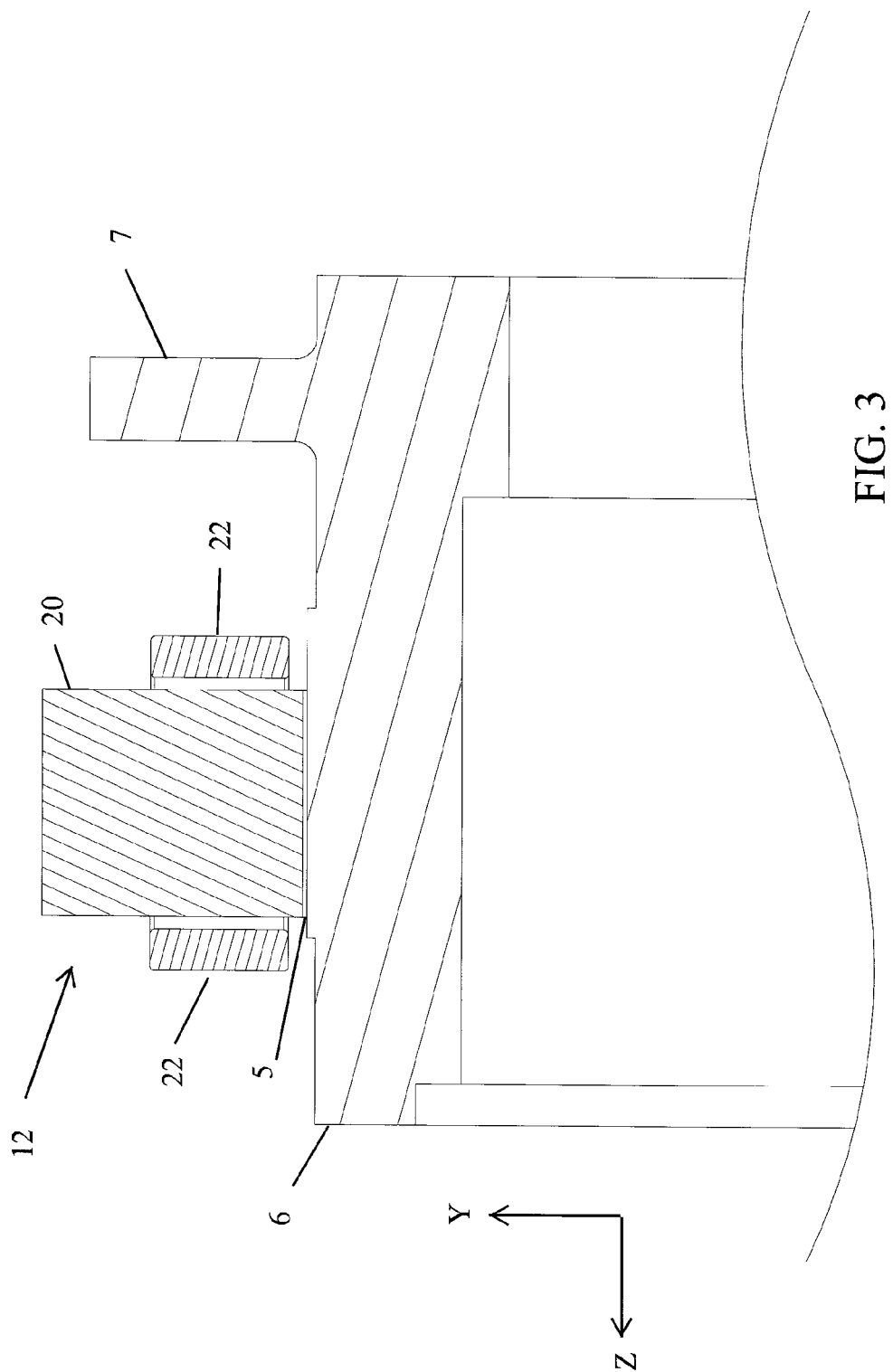
FIG. 3 shows a detailed cross-sectional view of a radial actuator shown in FIG. 1.

FIG. 3 shows a representative radial actuator 12 according to the first embodiment in greater detail. This radial actuator 12 comprises an electromagnet having at least one stator core 20 and at least one coil 22 wound around the core 20. Although the radial actuator 12 of this embodiment does not include a permanent magnet, such a design modification is possible. Further, although the cross-sectional drawing of FIG. 3 shows only a single core 20 and a single coil 22, each radial actuator 12 may comprise one or more coils 22 wound around one or more cores 20, as is shown in FIG. 1.

The radial actuators 12 are designed to adjust the position of the rotor 6 relative to the non-magnetic or auxiliary bearing(s) 28 in the X-Y plane during operation, i.e. in the radial direction of the rotor 6. Therefore, the radial actuators 12 are operated or controlled to ensure that the annular gap 5 is an appropriate distance or radial length while the rotor 6 is rotating, so that the rotor 6 does not contact the auxiliary bearing(s) 28. This ensures a friction-free rotation of the rotor 6 during operation.

For example, referring to FIG. 1, an ideal rotational axis 8' may be defined within the central bore of the gantry housing and preferably extends in the Z-direction. The ideal rotational axis 8' defines an axis of rotation that would provide an optimal or ideal spacing of the annular gap 5 between the rotor 6 and auxiliary bearing(s) 28 during operation. The respective radial actuators 12 are preferably individually controlled (as well as also lift actuator 10 if it optionally contains an electromagnet). In this case, the strength of the magnetic field generated by each respective radial actuator 12 is variably adjusted (as well as also lift actuator 10 if it optionally contains an electromagnet), such that the actual rotational axis 8 of the rotor 6 is aligned, or is substantially aligned, with the ideal rotational axis 8' during operation. That is, deviations between the actual and ideal rotational axes 8, 8' in the X-Y plane can be corrected or minimized by applying magnetic fields of different strengths to the rotor 6 via the radial actuators 12 (10), thereby pulling the rotor 6 in the appropriate direction to eliminate the deviation or at least substantially reduce the deviation.

Because the lift actuator 10 of this embodiment comprises only a passive magnetic source (i.e. permanent magnet 18), it is not actively controlled. However, the position of the rotor 6 in the X-Y plane is controlled or determined by the respective magnetic forces generated by the lift actuator 10 and the radial actuators 12. As was indicated above, if the lift actuator 10 includes a coil, then the lift actuator 10 can also actively participate in controlling the X-Y position of the rotor 6. For example, the coil can provide either a constant or temporary bias current or offset force during normal operation and/or during initial levitation of the rotor 6.

It should be understood that the distance between the ideal rotational axis 8' and the actual rotational axis 8 shown in FIG. 1 has been exaggerated for illustration purposes and is not to scale. In practice, the distance between the two axes 8, 8' is preferably equal to or less than about one millimeter.

At least a portion of the circumferential outer portion of the rotor 6 that is disposed adjacent to the lift actuator(s) and the radial actuator(s) 12 comprises a magnetically-permeable material. Further, because the two radial actuators 12 disposed on the upper left and upper right of the rotor 6 as shown in FIG. 1 may also perform a portion of the rotor-lifting work during operation, the two upper radial actuators 12 may be configured to generate a larger magnetic field than the two lower radial actuators 12. For example, the two upper radial actuators 12 shown in FIG. 1 may optionally also include a permanent magnet for passively lifting the rotor 6. However, all radial actuators 12 may be configured the same or substantially the same in other embodiments.

In another alternate embodiment, if the lift actuator 10 is designed to lift, e.g., more than the weight of the rotor 6, then the two lower radial actuators 12 may be larger in order to be able to pull down the rotor 6 away from the lift actuator 10.

The radial actuators 12 may be mounted on the gantry housing equidistantly or substantially equidistantly around the circumference of the rotor 6 or in another arrangement. In the embodiment shown in FIG. 1, the four radial actuators 12 are disposed in upper pair and a lower pair, wherein the two radial actuators 12 of each pair are separated by 90° from each other around the circumference of the rotor 6, i.e. 45° from a vertical axis extending through the central axis 8. The skilled person will recognize that various other configurations for the radial actuators 12 are possible depending upon the particular application of the present teachings and it is not necessary for radial actuators 12 to be oppositely disposed from each other.

Although not shown in FIG. 3, the magnetic flux path extends in a closed path, e.g., a substantially circular path, that extends generally in the X-Y plane (i.e. perpendicular to the view of FIG. 3) and goes through the stator core 20, across a clearance between the stator core 20 and the rotor 6 and through the adjacent portion of the rotor 6. The core of radial actuators 12 preferably comprise a plurality of laminations that are disposed adjacent to each other in the circumferential direction of the rotor 6, i.e. parallel to the flux path. This arrangement of the laminations has the advantageous effect of reducing eddy currents and improving dynamic control (dF/dt).

The embodiment of FIGS. 1-4 also includes three axial actuator pairs 14 mounted on the gantry housing. Two upper axial actuator pairs 14 are preferably disposed in a mirror-symmetric manner about a Y-Z plane that contains the ideal rotational axis 8'. The third axial actuator 14 is disposed at or near a bottom or vertically lowermost portion of the rotor 6. However, it should be understood that the axial actuators 14 need not be disposed in pairs and/or the upper axial actuator pairs 14 need not be disposed in a mirror-symmetric manner. Further, more or less than three axial actuators 14 can be used in certain embodiments of the present teachings.

Figure 4:
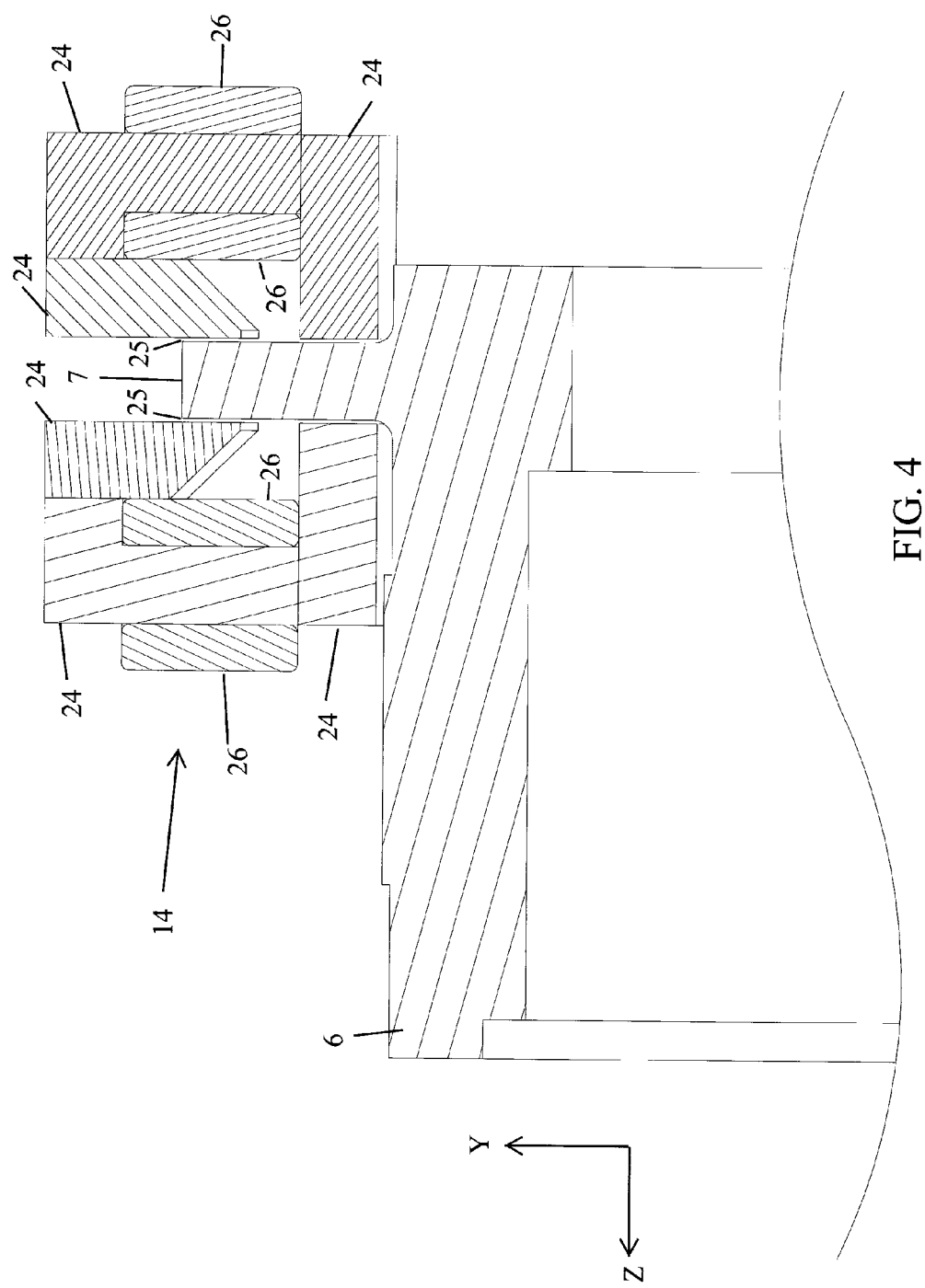
FIG. 4 shows a detailed cross-sectional view of an axial actuator shown in FIG. 1 and FIG. 5.

Referring to FIG. 4, a representative axial actuator pair 14 comprises a pair of stator cores 24, each having a coil 26 wound around it. The two sets of core 24 and coil 26 are disposed substantially in parallel with a spacing therebetween and are mounted on the gantry housing such that an annular flange 7 of the rotor 6 preferably extends in the radial direction within at least a portion of the radially-extending spacing.

The axial actuator pairs 14 are configured to variably adjust the position of the rotor 6 along the Z-direction, i.e. in the axial direction of the rotating rotor 6. That is, the axial actuators 14 are preferably individually controlled, i.e. the strength of the magnetic field generated by each respective set of stator core 24 and coil 26 is varied, so as to maintain the annular flange 7 substantially in the middle of the spacing between the pair of cores 24 and coils 26. For example, if the annular flange 7 (and thus the rotor 6) has drifted too far to the right in FIG. 4 (which corresponds to the rotor 6 moving into the page away from the viewer in the illustration of FIG. 1), the axial actuator pair 14 is controlled so that the force on the left side is greater than on the right side of FIG. 4, thereby pulling the annular flange 7 (and thus the rotor 6) to the left in FIG. 4.

Naturally, the design of the axial actuator 14 also may be modified without departing from the scope of the present teachings. For example, the cores 24 and coils 26 are not required to be disposed directly across from each other, such that a radially-extending spacing is defined between two sets of opposing cores 24 and coils 26. Instead, each set of one core 24 and coil 26 may be disposed around the circumference of the rotor 6 without a directly-opposing core 24 and coil 26. Furthermore, it is not necessary that equal numbers of cores 24 and coils 26 are disposed on opposite sides of the annular flange 7 in the Z-direction. However, it is generally preferred that at least one set of core 24 and coil 26 is disposed on each side of the annular flange 7 as viewed in the Z-direction, so as to enable the rotor 6 to be pulled or attracted by at least one actuator 14 in both directions along the Z-axis. Moreover, while homopolar axial actuators 14 are shown, heteropolar axial actuators could also be utilized.

Although not shown in FIG. 4, the magnetic flux path extends in a closed path, e.g., a substantially oval path, that extends generally in the Y-Z plane and goes through the various portions of the stator core 24, across the clearance 25 between the stator core 24 and the annular flange 7 and through the adjacent portion of the annular flange 7.

Also, the gap between the outer circumference 11 of the rotor 6 and the stator cores 24 of the axial actuator pair 14 is not necessarily shown to scale and may be relatively larger. In this case, the axial actuator pair 14 may be moved outward in the radial direction and the annular flange 7 may be extended farther in the radial direction so as to accommodate the larger gap between the rotor 6 and the cores 24.

Referring again to FIG. 1, at least one position sensor 9 is preferably disposed on the gantry housing around the circumference of the rotor 6. In this embodiment, four substantially equally-spaced position sensors 9 are utilized.

Each position sensor 9 is preferably configured to sense or detect the location of the rotor 6 in the X-Y (vertical) plane (radial direction) and/or along the Z-axis (axial direction). The position sensor(s) 9 is/are preferably non-contacting, inductive-type position sensors arranged in pairs to sense both axial and radial movement of the rotor 6. The signals generated by the position sensor(s) 9 are preferably transmitted to the magnetic bearing controller, which processes the signals and then adjusts the respective magnetic fields of at least the radial and axial actuators 12, 14 in order to correct any positional deviations of the rotor 6 from the ideal rotational axis 8' and/or the ideal position in the axial (Z) direction.

In addition, one or more auxiliary, non-magnetic bearings 28 are preferably mounted on the gantry housing for rotatably supporting the rotor 6, e.g., as a fail-safe in the event of a system fault or a power outage. In a further optional embodiment, one or more of the auxiliary bearings 28 may also perform a part of the function of rotatably supporting the rotor 6 during operation, although it is preferred that the actuators 10, 12, 14 perform all of the rotor-supporting work during operation so that the rotation of the rotor 6 is friction-free.

The auxiliary bearing(s) 28 may be embodied as one or more plain bearings, e.g., sleeves, bushings or journals, or may be one or more rolling-element bearings, e.g., ball bearings, angular contact bearings or cylindrical roller bearings. The auxiliary bearing(s) 28 may continuously extend all the way around the circumference of the rotor 6, e.g., the auxiliary bearing 28 may be embodied as a single, large bearing that completely encircles and rotatably supports the entire rotor 6. In the alternative, the auxiliary bearing 28 may comprise one or more individual elements, such as discrete ball bearings 28 as shown in FIG. 1 or discontinuous sections of a plain bearing. Optionally, the auxiliary bearing(s) may also include one or more radial air bearings.

As indicated in FIG. 1, the auxiliary bearings 28 optionally may be embodied as deep-groove ball bearings 28 mounted to the gantry housing and may be disposed in a mirror-symmetric manner about a Y-Z plane that contains the ideal rotational axis 8'. However, it is understood that the auxiliary bearings 28 also may be disposed equidistantly about the rotor 6 or as shown in FIG. 1 with the upper and lower auxiliary bearings 28 being relatively closer to each other.

It is also preferred that the auxiliary bearing(s) 28 has/have a radially-inward-facing bearing surface with a inner diameter that is slightly greater than an outer diameter of a radially-outermost portion of the rotor 6, which is disposed adjacent the radially-inward-facing bearing surface of the auxiliary bearing(s) 28. Thus, in normal operation, the slight difference in diameters means that no portion of the rotor 6 contacts the auxiliary bearing(s) 28 while the rotor 6 is rotating. However, in the event, e.g., that one or more of the actuators 10, 12, 14 malfunction(s), an outer portion of the rotor 6 may safely contact the auxiliary bearing(s) 28 and the auxiliary bearing(s) 28 will support the rotation of the rotor 6 at least temporarily, e.g., while the rotor 6 is slowing down.

Herein, it is noted that the width of the annular gap in the radial direction between the outer circumference 11 of the rotor 6 and the auxiliary bearing(s) 28 mounted on the stationary gantry housing is preferably less than the width of the annular gap in the radial direction between the outer circumference 11 of the rotor 6 and the lift actuator(s) 10, the radial actuator(s) 12 and/or the position sensor(s) 9 mounted on the stationary gantry housing. In this case, the lift actuator(s) 10, the radial actuator(s) 12 and/or the position sensor(s) 9 is/are prevented from ever contacting the rotor 6, thereby protecting these components, e.g. in the event of a system malfunction. In a preferred embodiment, the width of the annular gap relative to the auxiliary bearing(s) 28 may be, e.g., about one-half of the width of the annular gap relative to the lift actuator(s) 10, the radial actuator(s) 12 and/or the position sensor(s) 9.

In addition or in the alternative, it may be appropriate to also place one or more auxiliary bearings on each axial side of the annular flange 7 and/or on each axial side of the main body of the rotor 6, which auxiliary bearings would bound or limit the range of movement of the rotor 6 in the axial or Z direction. In this embodiment as well, the width of the gap or spacing in the axial direction between such auxiliary bearing(s) and the annular flange 7 and/or the main body of the rotor 6 is preferably less than the width of the gap 25 between each side of the axial actuator pair 14 and the annular flange 7, more preferably about one-half of width of the gap 25. In this case, the axial actuator(s) 14 (in particular the stator core 24) would be prevented from ever contacting the rotor 6. Such auxiliary bearing(s) may be selected from any of the auxiliary bearings described herein, such as, e.g., plain bearings or rolling-element bearings. In a preferred embodiment discussed further below, a linear or curved bearing attached to one of the gantry housing or the rotor 6 may function, e.g., together with a ring shaft attached to the other of the gantry housing or the rotor 6, to limit or bound, at least partially, movement of the rotor 6 in the axial or Z-direction.

In preferred embodiments, the lift actuator 10 is a passive homopolar radial actuator having a rated force-generating capacity of between about 5-15 kN (kilonewtons), more preferably between about 7-12 kN, the radial actuators are active heteropolar actuators having a rated force-generating capacity of between about 1.5-5.5 kN, more preferably between about 1.5-4.5 kN, e.g., about 1.8 kN; the axial actuators are active heteropolar actuator pairs having a rated force-generating capacity of between about 0.5-6.0 kN, more preferably between about 1.0-5.0 kN, e.g. about 1.08 kN. Such specifications would be suitable for a rotor 6 having a diameter of about one meter and a weight of about 1000 kg. Naturally, these specifications may be varied to adapt the present teachings to other applications.

A second representative computed tomography machine 1' will be described with reference to FIGS. 5-7. Only differences with respect to the first representative embodiment will be discussed in detail, such that elements or features that are the same for the two embodiments need not be further discussed. Further, although a radiation source 2 and radiation detector 3 are not shown in FIG. 5, it is understood that one or both devices 2, 3 also may be mounted on the rotor 6 of the second representative embodiment.

Figure 5:
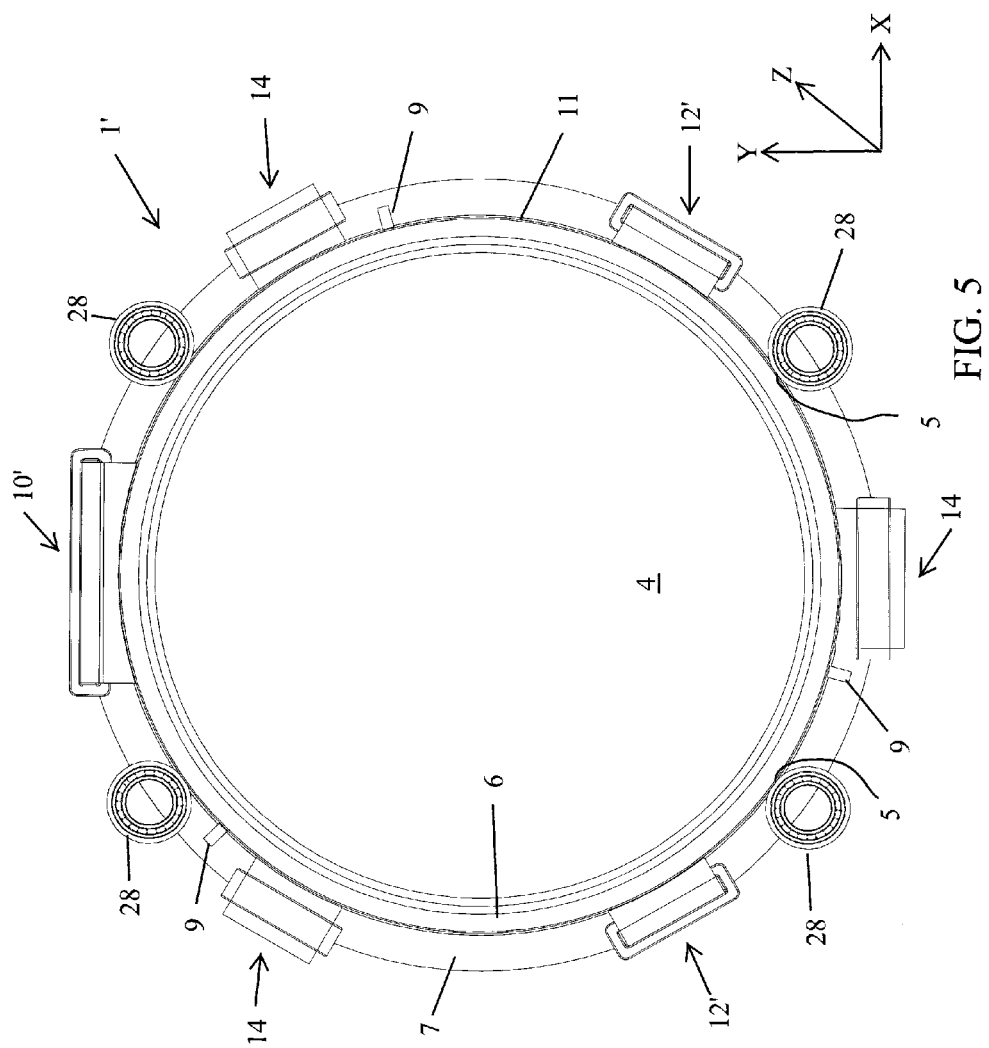
FIG. 5 shows an elevation view of a second representative embodiment of the present teachings.

FIG. 5 shows the computed tomography machine 1' in the X-Y plane. It is again understood that the Z-axis extends perpendicular to the sheet of the drawing. With respect to the arrangement of the actuators 10, 12, 14, the second representative embodiment differs from the first representative embodiment in that only two radial actuators 12' are provided around the lower half of the rotor 6, as the two upper radial actuators 12 shown in FIG. 1 have been omitted. Furthermore, only three position sensors 9 are utilized in the second representative embodiment instead of four and the upper and lower auxiliary bearings 28 have been spaced slightly farther apart than in FIG. 1.

Figure 6:
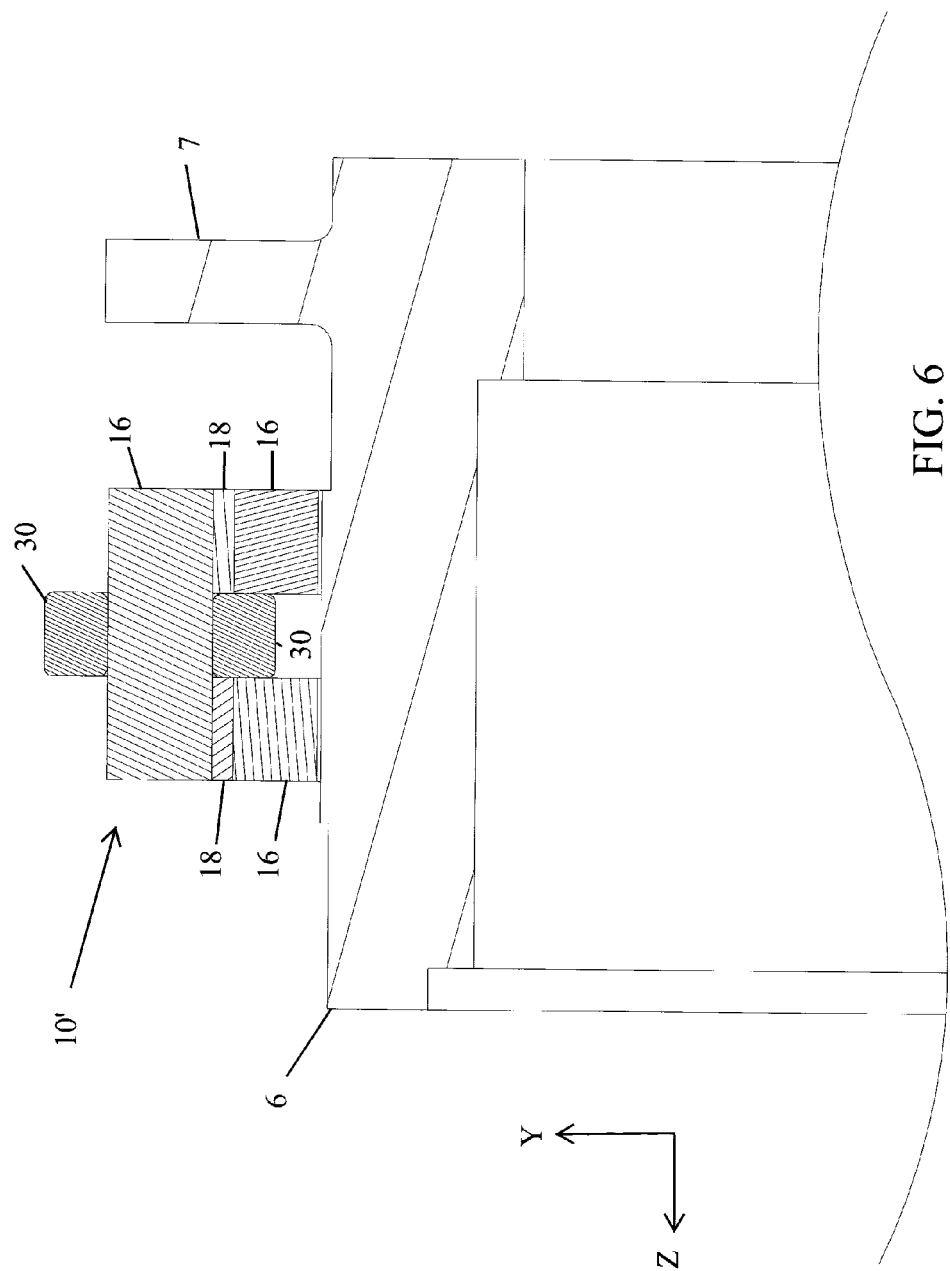
FIG. 6 shows a detailed cross-sectional view of a lift actuator shown in FIG. 5.

FIG. 6 shows a modified lift actuator 10' that may be utilized in either of the embodiments. This lift actuator 10' differs from FIG. 2 in that it contains a coil 30 wrapped around the stator core 16. Thus, the lift actuator 10' is an active actuator, which can generate a variable magnetic field in addition to the passive, permanent magnet field generated by the permanent magnet 18.

In such an embodiment, the electromagnet (coil 30 and core 16) may perform a portion of the rotor lifting work during operation, thereby supplementing the rotor-lifting force generated by the permanent magnet 18. However, in an alternate embodiment, the electromagnet may generate a field that cancels a portion of the magnetic flux generated by the permanent magnet 18.

The magnetic flux path of the lift actuator 10' of FIG. 6 extends in substantially the same manner as the magnetic flux path for the lift actuator 10 of FIG. 2.

FIG. 7 shows a modified radial actuator 12' that also may be utilized in either of the embodiments. In FIG. 7, the coil 34 is wrapped around the stator core 32 in the X-Y plane.

In the radial actuator 12' of FIG. 7, the magnetic flux path extends in a closed path, e.g., a substantially circular path, that extends generally in the Y-Z plane and goes through the various portions of the stator core 32, across the gap between the stator core 32 and the rotor 6 and though the adjacent portion of the rotor 6.

The axial actuator 14 of FIG. 4 may be utilized in the second representative embodiment without modification. In the alternative, the axial actuator 14 may be heteropolar.

The following description is applicable to both the first and second representative embodiments, as well as modifications thereof.

The inner diameter of the hollow interior 4 of the rotor 6 is preferably about one meter, although larger or smaller diameters may be appropriate depending upon the particular application of the present teachings. Further, the system 1, 1' is preferably designed to permit rotational speeds of about 300 revolutions per minute, although faster or slower speeds are also encompassed by the present teachings. For example, rotational speeds of up to about 1200 revolutions per minute or even up to 2000 revolutions per minute are contemplated in certain embodiments of the present teachings.

The stator cores of the various actuators are preferably laminated homopolar cores, but solid cores and/or heteropolar cores are also contemplated. The first representative embodiment of FIGS. 1-4 preferably uses a mixture of homopolar and heteropolar actuators, whereas the second representative embodiment of FIGS. 5-7 may use all homopolar actuators. Generally speaking, it is understood that solid cores and rotors have lower manufacturing costs, but laminated cores and rotors provide performance advantages. The skilled person is free to select the most appropriate actuators based upon the particular application of the present teachings.

The rotor 6 may also be solid or laminated. In one embodiment, a laminated rotor 6 may be used with heteropolar radial actuators, which would provide high dynamic control.

The actuators 10, 12, 14 may be controlled using standard magnetic bearing controllers known in the art, which generally provide ten amplifiers for ten actuators. For example, the actuator control may be performed by a magnetic bearing controller available from SKF, Inc. having model no. MB4160.

A representative control process may begin with measurement of the rotor position in both the radial and axial directions using the position sensors 9. The signals from sensors 9 are transmitted to the magnetic bearing controller, which compares the signals to one or more values representing the ideal position of the rotor 6 in the radial and axial directions. The ideal position may be programmed or input into the controller during machine start-up or initialization, or dynamically during machine operation. Any difference between the actual position and the ideal position results in the calculation of the change in current or force necessary to pull the rotor back to the ideal position. This calculation is translated into a command to the power amplifiers respectively connected to the coils of the respective actuators. The command may preferably comprise an instruction to increase or decrease current flow to one or more of the respective coils. If the current to a particular coil is increased, magnetic flux through the actuator and adjacent portion of the rotor increases, thereby increasing the force between the rotating and stationary components. As a result, the rotor will move toward the particular actuator along the axis of control. Application of differing magnetic fluxes to the rotor 6 will be additive in the different directions with the direction of movement of the rotor 6 corresponding to a vector thereof.

Although a single lift actuator 10, 10' is shown in the two representative embodiments, it is understood that the lift actuator function could be separated into two or more lift actuators 10, 10'. For example, two lift actuators 10, 10' could be mounted to an upper half of the gantry housing in a mirror-symmetric manner about a Y-Z plane containing the ideal rotational axis 8'. The resulting lift vector generated by the two lift actuators 10, 10' is thus preferably in the vertical or substantially vertical direction.

For point of reference, representative, but non-limiting dimensions for various elements of a representative CT machine 1 will be provided. For example, the rotor 6 preferably may have a radial width of about 25 millimeters and a depth in the Z-direction of about 81 millimeters. The stator cores 24 of the axial actuators 14 may have a radial width of about 50 millimeters and a depth in the Z-direction of about 30 millimeters. The gap 25 (see FIG. 4) between the stator core 24 and the annular flange 7 is preferably or ideally maintained during operation at about one millimeter on each side of the annular flange 7 in the Z-direction. The lift and/or radial actuators 10, 12 preferably may have a radial width of about 57 millimeters and a depth in the Z-direction of 60 millimeters.

The actuators 10, 10', 12, 12' preferably have a curvature on the side facing the rotor 6 that corresponds to the outer contour of the rotor 6, i.e. the rotor-facing sides are semicircular. This means that the rotor-facing side of the magnet and/or the stator core is preferably semi-circular. The axial actuator 14 is preferably straight, although curved configurations are also possible.

The bearing and sensor surfaces on the rotor 6 may be laminated and/or solid. The rotor 6 may be constructed as a single, integral component (i.e. a one-piece construction) or may be an assembly of several pieces, each comprised of magnetic and/or non-magnetic materials.

The first and second representative embodiments provide five axes of active control. In the alternative, one or more of the axes may be levitated passively (i.e. no active control) or may be controlled mechanically with a permanently-engaged rolling element, sliding or air/hydrodynamic bearings or any other type of bearing(s).

At least the radial and axial actuators 12, 14 (as well as the lift actuator 10 if it has an electromagnet) are preferably controlled according to a closed loop feedback using signals from the position sensors 9 to adjust the gantry/rotor position. As non-limiting examples, the control may be based upon independent axis control (SISO—single input, single output) or combined axis control (MIMO—multiple input, multiple output).

While all of the actuators 10, 12, 14, sensors 9 and auxiliary bearings 28 are shown as generally falling within a single X-Y plane, naturally the various components may be located in two or more X-Y planes, each separated by an axial distance. If multiple vertical planes of components are utilized, each vertical plane may have the same, less or more components (e.g., bearings, sensors, etc.) as any other plane.

The system 1 may include an integrated rotational motor, with or without electrical contacts (e.g., brushes) between the rotor 6 and the stationary components.

An uninterrupted power supply may be utilized to improve system robustness.

The present teachings also may be easily modified for an annular rotor 6 that is rotated about a vertical or a substantially vertical rotational axis, which means that the rotational plane of the rotor 6 is horizontal or substantially horizontal. In this case, at least one lift actuator is disposed above the annular rotor to vertically lift the annular rotor at least while it rotates. For example, two or more lift actuators may be disposed substantially equidistantly away from each other around the outer circumference of the annular rotor 6 or the annular flange 7. Because the lift actuators influence the position of the rotor 6 in its axial direction (i.e. the axial direction of the rotor 6 extends in the vertical direction), the lift actuators may preferably perform at least a part of the function of the above-described axial actuators 14 and may be constructed in substantially the same way as the axial actuator 14 of FIG. 3, although it is preferred that at least one permanent magnet is provided on the vertically upper side of the rotor 6 in order to provide passive lifting capacity, which would improve the overall system efficiency.

Thus, the lift actuators may be combined with the axial actuators, such that one or more pairs of actuators are provided, preferably equidistantly around the circumference of the annular rotor 6. As a result, the lift/axial actuators of such an embodiment would be capable of pulling the rotor 6 up and down in the vertical direction.

In such an embodiment, at least one radial actuator influences the position of the rotor 6 in the radial direction of the rotor 6. Again, it is preferable to dispose at least three radial actuators around the outer circumference of the rotor 6 and such radial actuators may be constructed in a similar fashion to the radial actuators 12, 12' of FIGS. 3 and 7.

In another modification of the present teachings, one or more of the magnetic actuators 10, 10', 12, 12', 14 may be replaced by a non-magnetic bearing. For example, it would be possible to use magnetic bearings for controlling the position of the rotor 6 in its axial direction, while non-magnetic bearings (e.g., bushings or rolling-element bearings) rotatably support the outer circumferential surface of the rotor 6 in the radial direction thereof. In addition or in the alternative, the rotor 6 may be axially supported or guided by one or more non-magnetic bearings and magnetic bearings may be used to rotatably support the rotor 6 in the radial direction during operation. Thus, in certain embodiments, one or more of the lift actuator, radial actuator and/or axial actuator (axial actuator pair) may be replaced with any one or more of the non-magnetic bearings that are disclosed herein above or below. For purposes of conciseness, it is understood that any of the non-magnetic bearings disclosed herein are suitable replacements for the lift, radial and/or axial actuators (magnetic bearings) and all respective combinations of magnetic and non-magnetic bearings are disclosed hereby.

The present teachings are not particularly limited to CT machines and may be preferably utilized with any rotor application, in which the rotational axis of the rotor 6 is substantially in the horizontal or vertical plane, although various degrees of tilting therefrom are also contemplated. The rotor 6 may be solid or substantially solid or the rotor 6 may be tubular, e.g., it may have an at least partially hollow interior.

Although the preferred radiation source for the computed tomography image system is an x-ray source, other radiation sources and corresponding detectors may be utilized to achieve, for example, positron emission tomography, electron beam tomography or single photon emission computed tomography. Further, other sources of radiation may be attached to the rotor for other applications, such as sources of ionizing or non-ionizing radiation, including e.g. lasers. The present teachings are widely applicable to any application that utilizes a high-speed rotor to carry a device that operates in a non-contacting manner while being rotated relative to a target object.

Although a variety of non-magnetic auxiliary bearings 28 may be utilized as a 'back up' in case of a system or a power failure, as was described above, another possibility is a linear bearing, such as a linear ball bearing available from SKF, Inc. under model number LBBR25. In principle, the function of the auxiliary bearing(s) 28 is to prevent the rotor 6 from ever directly contacting the gantry housing and also to at least temporarily support rotation of the rotor 6 in case the rotating rotor 6 unintentionally touches the bearing(s) 28 during operation or when the system is not functional (e.g., power off). For example, if one or more of the magnetic actuators 10, 10', 12, 12', 14 fails to function properly during operation, there will be no damage to the rotor 6 caused by the moving rotor 6 contacting the stationary housing, because the rotor 6 will be rotatably supported by the auxiliary bearing(s) 28 at least temporarily.

A linear ball bearing generally involves a tubular housing structure, e.g., a bushing, having a plurality of closed-loop grooves, e.g., recirculating ball tracks, formed or defined on an inner surface thereof or formed in a bearing cage disposed within the bushing. Each closed-loop groove has a pair of parallel grooves or tracks extending in the longitudinal direction of the linear bearing. The straight grooves or tracks are connected at each end by a curved, e.g., semi-circular, groove or track, e.g., a deflection track. Ball bearings are rotatably and movably disposed within each of the closed-loop grooves and support a cylindrical shaft that extends through the tubular structure. When the cylindrical shaft moves in the longitudinal direction of the linear bearing relative to the tubular structure, the ball bearings circulate around each closed-loop groove or track. The ball bearings on one longitudinal side of the closed-loop groove support the linear movement of the cylindrical shaft and act as load-bearing balls. The ball bearings on the other longitudinal side of the closed-loop groove do not support the load (i.e. non-load-bearing balls) and move in the opposite direction of the movement direction of the cylindrical shaft. Therefore, the depth on the non-supporting longitudinal side of the closed-loop groove is deeper than on the load-bearing longitudinal side. The bearing balls disposed on the non-load bearing side are not required to be exposed to the inner surface of the tubular surface and, e.g., may be covered by a metal plate structure.

In addition, the load-bearing side of the closed-loop groove may be reinforced with a load or track plate, e.g., a metal plate structure, disposed between the ball bearings and the tubular housing structure. Further, the tubular housing structure may be hardened plastic or metal, preferably metal, such as steel in the presently preferred applications.

Further teachings concerning a representative linear bearing can be found in U.S. Pat. No. 6,168,313, which is incorporated herein by reference.

In a further embodiment of the present disclosure, a torus-shaped or toroidal structure, preferably a ring torus, is mounted to one of the rotor 6 or the gantry housing. Linear ball bearings may be mounted to the other of the rotor 6 and the gantry housing. The torus-shaped structure extends through the linear ball bearings and is preferably comprised of a metal. The torus-shaped structure may be a hardened wire structure.

It is preferred that the linear ball bearings are mounted onto the rotor 6 so as to rotate therewith. In this case, the shaft of the torus-structure is fixedly mounted on or attached to the gantry housing and the shaft has an outer diameter that is slightly smaller than the inner diameter of the linear ball bearing. Preferably, the outer diameter of the shaft is selected such that the annular gap or clearance between the shaft of the torus structure and each longitudinal end of the linear bearing is smaller than the gap between the rotor and the magnetic bearings/actuators, i.e. when the magnetic bearings are levitating and rotatably supporting the rotor 6. During normal operation, the torus-shaped structure preferably does not contact the linear ball bearings so as to permit friction-free rotation of the rotor 6.

Although the balls of the linear ball bearing may be metal, such as steel, it is preferred that the balls comprise or substantially consist of a ceramic material, e.g., bearing-grade silicon nitride. In addition, the ball recirculation mechanism of the linear ball bearing is preferably reinforced to such a degree as to allow for the instantaneous acceleration from zero to 10 meters per second in case the torus-shaped structure comes into contact with the linear ball bearings, i.e. touches down, while the rotor 6 is rotating at top speed, e.g., about 300 revolutions per minute, although other top rotational speeds are contemplated.

Figure 8B:
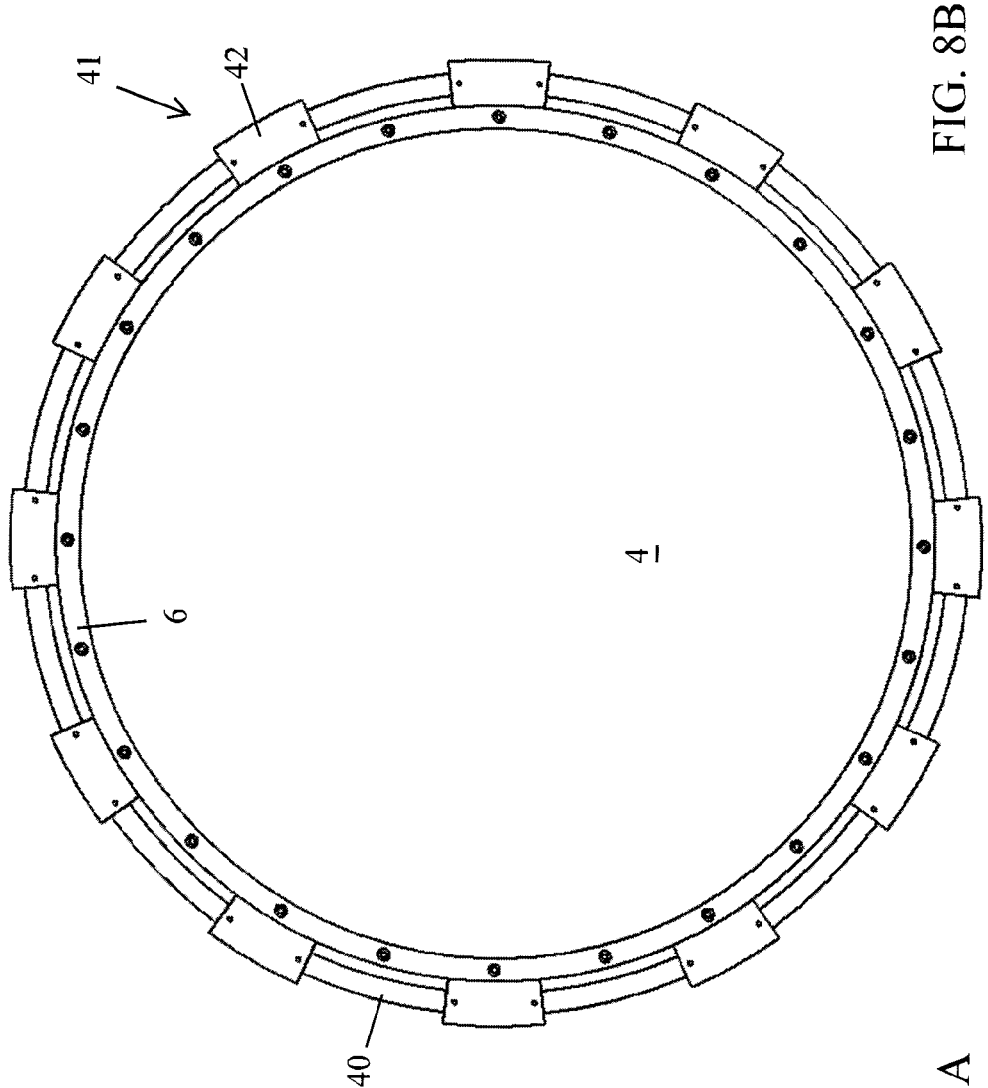
FIG. 8B shows an elevation view of the curved bearing arrangement as viewed along the axial direction of the annular rotor.
Figure 8A:
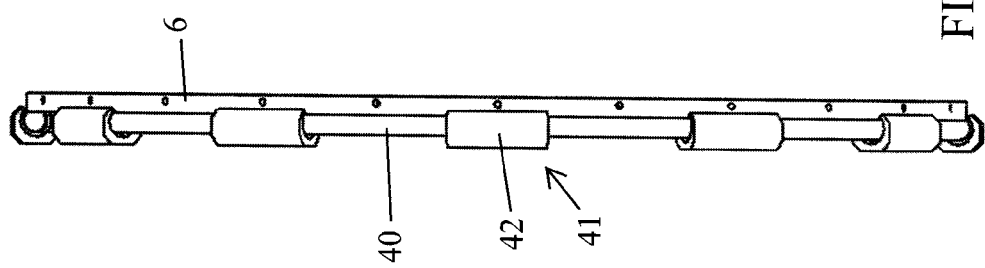
FIG. 8A shows a side view of a representative curved bearing arrangement for supporting or supplementally supporting an annular rotor.
Figure 9:
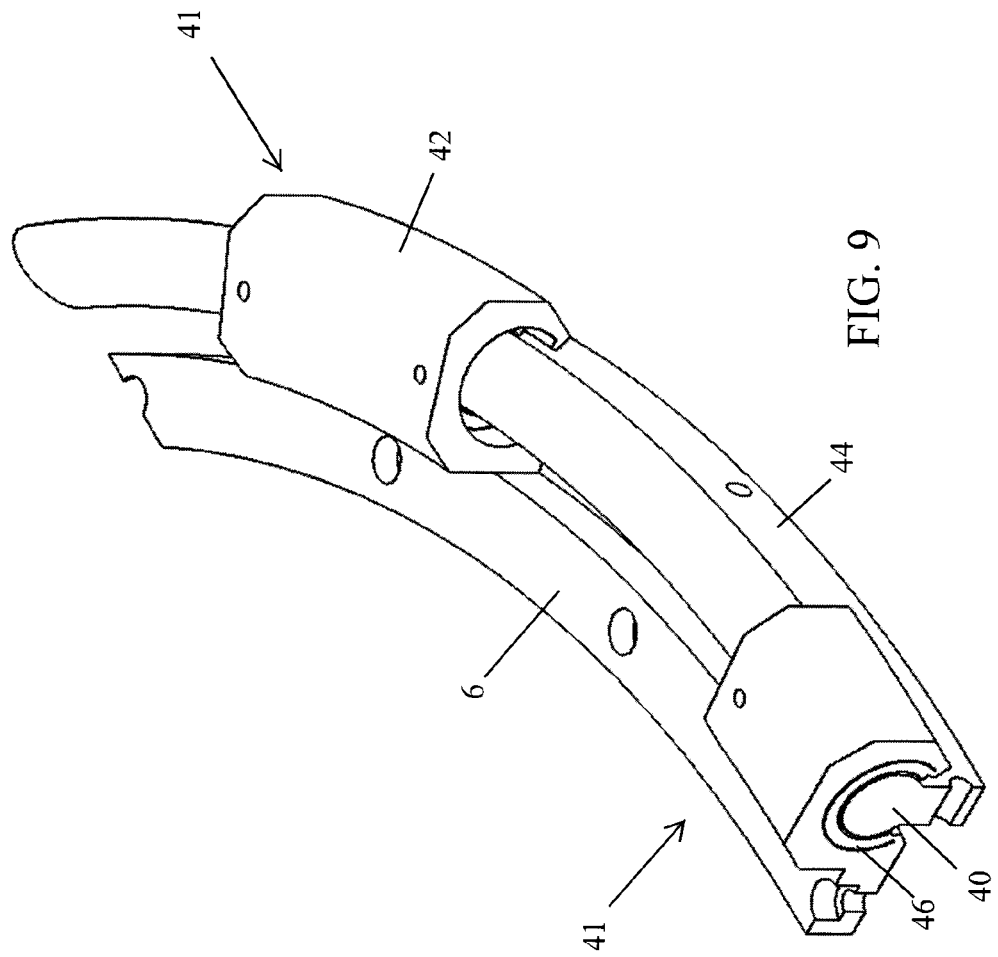
FIG. 9 shows a perspective view of a portion of the curved bearing arrangement of FIGS. 8A and 8B.
Figure 10:
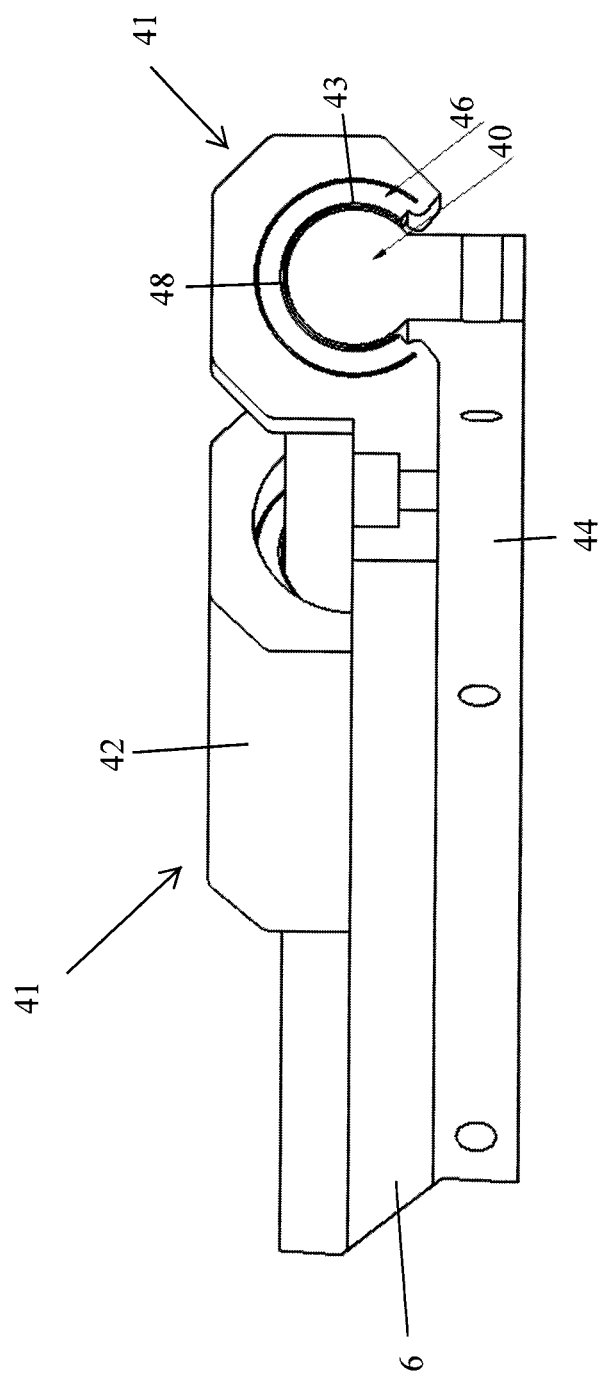
FIG. 10 shows another perspective view of a portion of the curved bearing arrangement of FIGS. 8A and 8B.

In a modification of the above-described linear ball bearing embodiment, the tubular housing structure 42 supporting the balls may be curved, thereby forming a curved, tubular ball bearing 41 as shown in FIGS. 8-10. The curved tubular housing structure 42 preferably has the same, or substantially the same, curvature as a generally torus-shaped shaft 40 movably disposed therein. Further, the shaft 40 preferably has an outer diameter that is slightly less than an inner diameter of the ball bearing cage 46 so that an annular clearance 48 is present between the shaft 40 and the inner surface 43 of the curved bearing 41 when the rotor 6 is being rotated under the guidance of the above-describe magnetic bearing system. During normal operation, the annular clearance 48 is preferably at least substantially constant along the entire length of each curved bearing 41 and the portion of the shaft 40 disposed therein.

A plurality of curved bearings 41 (e.g., twelve as shown in FIG. 8B) may be affixed to the rotor 6 in equally-spaced intervals. The shaft 40 is movably supported by the curved bearings 41 and is affixed to the stationary gantry housing via an annular connecting flange 44 (see FIGS. 9-10). The connection of the flange 44 and thus the shaft 40 to the stationary gantry housing is not shown in the drawings for purposes of simplicity and clarity.

However, it should be understood that this bearing/shaft arrangement may be reversed such that the shaft 40 is affixed to the rotor 6 so as to rotate therewith and the curved bearings 41 are affixed to the stationary gantry housing.

In another modification of the above-described linear ball bearing, the grooves or tracks of the bearing cage 46 of the curved bearing 41 may be designed such that the non load-bearing ball path is disposed radially outward of the load-bearing path, instead of curving around the circumference of the shaft 40. For example, a metal load plate, which provides support for the load-bearing balls, may be disposed between the load-bearing balls and the non load-bearing balls. In this case, after supporting the load (i.e. contacting the ring shaft 40), the balls would circulate or move along a first curved path that is directed radially outward from the load-bearing path, then along the non-load bearing path (disposed directly radially outward of the load-bearing path) and finally along a curved path extending radially inwardly to reach the load-bearing path again. Thus, the balls would move up a ramp to come into contact again with the ring shaft 40, instead of moving around a corner or curved path as is typical in linear bearings. In this embodiment, the load-bearing path and non load-bearing path are preferably both curved and the two curves are preferably concentric. The two curves are also disposed in the same plane, which extends in the radial direction of the rotor 6.

The non load-bearing path may be configured substantially as a curved tube defined within the tubular structure, which is again preferably constructed from a metal material, such as steel.

The roller bodies optionally may be cylindrical in such an embodiment.

In a further modification of either of the above-described linear and curved ball bearings, the linear or curved ball bearing is not required to be enclosed in the circumferential direction. Rather, as shown most clearly in FIG. 10, an opening of about 100°, e.g., between 90-120°, may extend along one longitudinal side of the curved or linear bearing, e.g. along a side opening towards the axial or Z-direction of the rotor 6. Such an opening would permit the ring shaft 40 to be easily mounted in and removed from the curved or linear bearing by moving the shaft 40 in the axial or Z-direction of the rotor 6. For example, the opening may be sized so that the ring shaft 40 snap-fits through the opening in the side of the curved or linear bearing when the ring shaft 40 is mounted in the curved or linear bearing. Thus, the size of the opening in the circumferential direction of the curved or linear bearing is preferably slightly smaller than the outer diameter of the ring shaft 40.

If a curved bearing 41 is provided with such a side-opening, the bearing cage 46 is preferably provided with five closed-loop ball circulation paths, such that there are five load-bearing ball tracks for contacting the ring shaft 40. Such a curved bearing 41 preferably has a static load capacity of about 1500 Newtons for the above-described CT application. In a further embodiment, two curved ball bearings 41 may be utilized at each bearing point and the bearing points may be spaced approximately 15° apart, thereby providing twelve bearing points around the circumference of the rotor 6. Each bearing cartridge 41 may have a length of approximately 15-30 centimeters, more preferably 20-25 centimeters, although the particular length will depend upon application-specific parameters.

Figure 11:
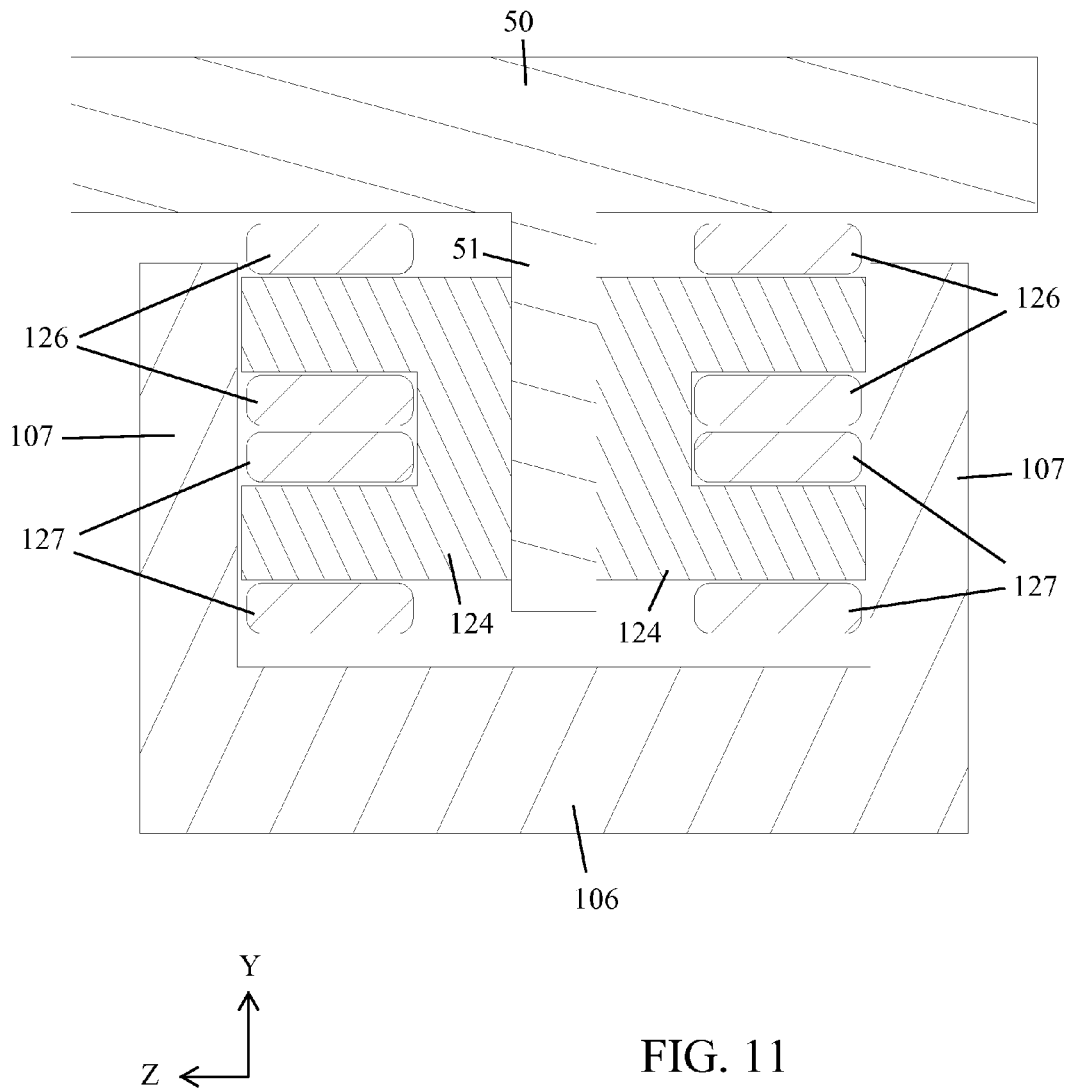
FIG. 11 shows a cross-section through a third representative embodiment of the present teachings.

Turning now to FIG. 11, a modification of the above-described rotor and axial actuator pair(s) will now be described, which modification may be advantageously utilized with any of the preceding or subsequent embodiments disclosed herein.

FIG. 11 shows cross-section through a portion of the stationary housing (frame) 50, which has at least one annular mounting flange 51 that extends radially-inward from the housing 50.

FIG. 11 further shows a modified rotor 106 that has substantially a U-shape in the Y-Z cross-section. That is, the rotor 106 includes a pair of radially-outward-extending, annular flanges 107 that are spaced apart and extend at least substantially parallel to each other. Thus, a hollow space or well is defined in the axial (Z) direction between the two annular flanges 107.

Similar to the preceding embodiments, each annular flange 107 comprises, at least in part, a magnetically-permeable material disposed on or proximal to an outer circumference of the annular rotor 106.

Although the annular flanges 107 are shown as being disposed at the opposite longitudinal edges of the rotor 106 in the Z-direction (longitudinal direction), naturally the annular flanges 107 may be disposed inward of the respective longitudinal edges of the rotor 106. Also, while the annular flanges 107 are shown as being entirely parallel to each other, the flanges 107 may be modified to other non-parallel structures attached to or extending from the respective flanges 107. However, the flanges 107 are preferably constructed in a mirror-symmetric manner with respect to a vertical axis extending in the Y direction between the flanges 107 in order to provide a balanced structure in the Z direction.

The rotor 106 and flanges 107 are preferably formed, e.g., such that the rotor 106 and one of the flanges 107 are integrally formed (i.e. with no seam therebetween) and the other flange 107 is formed as a removable plate (ring) that is detachably attachable to the rotor 106. However, it is also possible to integrally form both flanges 107 with the rotor 106 or to form both flanges 107 as removable plates (rings).

Similar to the preceding embodiments, at least one axial actuator pair is provided and comprises a pair of stator cores 124, each having at least one coil 126 wound around it. However, in the present embodiment, the two stator cores 124 are fixedly mounted onto opposite axial sides of the annular mounting flange 51 of the stationary housing 50. That is, the two sets of core 124 and coil 126 are disposed substantially in parallel with a spacing therebetween and are mounted on the annular mounting flange 51 such that the coils 126 are respectively associated with, i.e. disposed proximal to, the two annular flanges 107 of the rotor 106. As in the preceding embodiments, a small gap is provided between the axially outermost portion of each stator core 124/coil 126 and the adjacent flange 107 so that there is no contact between these parts, especially when the rotor 106 is rotating at high speed.

In the embodiment shown in FIG. 11, a second coil 127 is provided to add to the flux created by the first coil 126, such that coil 126 creates a North (or South) pole on its associated stator core 124 arm, and coil 127 creates a South (or North) pole on its associated stator core 124 arm, the coils 126 and 127 creating magnets of opposite polarity. In so doing coils 126 and 127 work together as a pair to create a stronger magnetic field in the gap between the flange 107 and core 124.

Similar to the preceding embodiments, the two axial actuators of FIG. 11 are configured to variably adjust the position of the rotor 106 along the Z-direction, i.e. in the axial direction of the rotating rotor 106. That is, the coils 126, 127 on a respective stator core 124 are preferably controlled, i.e. the strength of the magnetic field generated by each respective stator core 124 and coil 126, 127 is varied, so as to maintain the annular mounting flange 51 substantially in the middle of the spacing between the pair of rotor annular flanges 107 with the respective gaps on each side of the axial actuators.

For example, if the annular flanges 107 (and thus the rotor 106) drift or move too far to the right in FIG. 11 (which corresponds to the rotor 106 moving into the page away from the viewer in the illustration of FIG. 1), the coils 126, 127 are controlled so that coils 126, 127 on the right-side pull more strongly than the coils 126, 127 on the left-side, whereby the annular flanges 107 (and thus the rotor 106) will be moved to the left in FIG. 11. It is noted that the lift actuator(s) 10, 10' and radial actuator(s) 12, 12' are also preferably fixedly mounted onto the annular mounting flange 51 and are thus disposed within the well defined by the U-shaped rotor 106 and annular flanges 107.

The embodiment of FIG. 11 provides the following advantages as compared to the preceding embodiments.

First, the design of the rotor and housing can be made more compact in the axial or longitudinal (Z) direction of the CT machine, because the pair of axial actuator(s) (i.e. both coils 126 (127) and stator cores 124) are disposed within the axial length of the rotor 106. That is, there is no axial overhang of one stator core 124 and coil 126 as can be seen on the right-side of FIG. 4.

Second, by utilizing two annular flanges 107, warping of the rotor 106 during high-speed rotation can be reduced, because the two annular flanges 107 act as a reinforcing device that improves the overall stiffness or rigidity of the rotor assembly.

Third, by utilizing two annular flanges 107 that surround the coils 126, 127 and stator cores 124, better magnetic shielding results, because the magnetic fields generated by the axial actuator pairs (as well as by the lift actuator(s) 10, 10' and the radial actuator(s) 12, 12') will be contained by the surrounding structures, i.e. the housing 50, rotor 106 and flanges 107. Therefore, stray magnetic flux is less likely to interfere with any other equipment in the vicinity of the CT machine.

Figure 12:
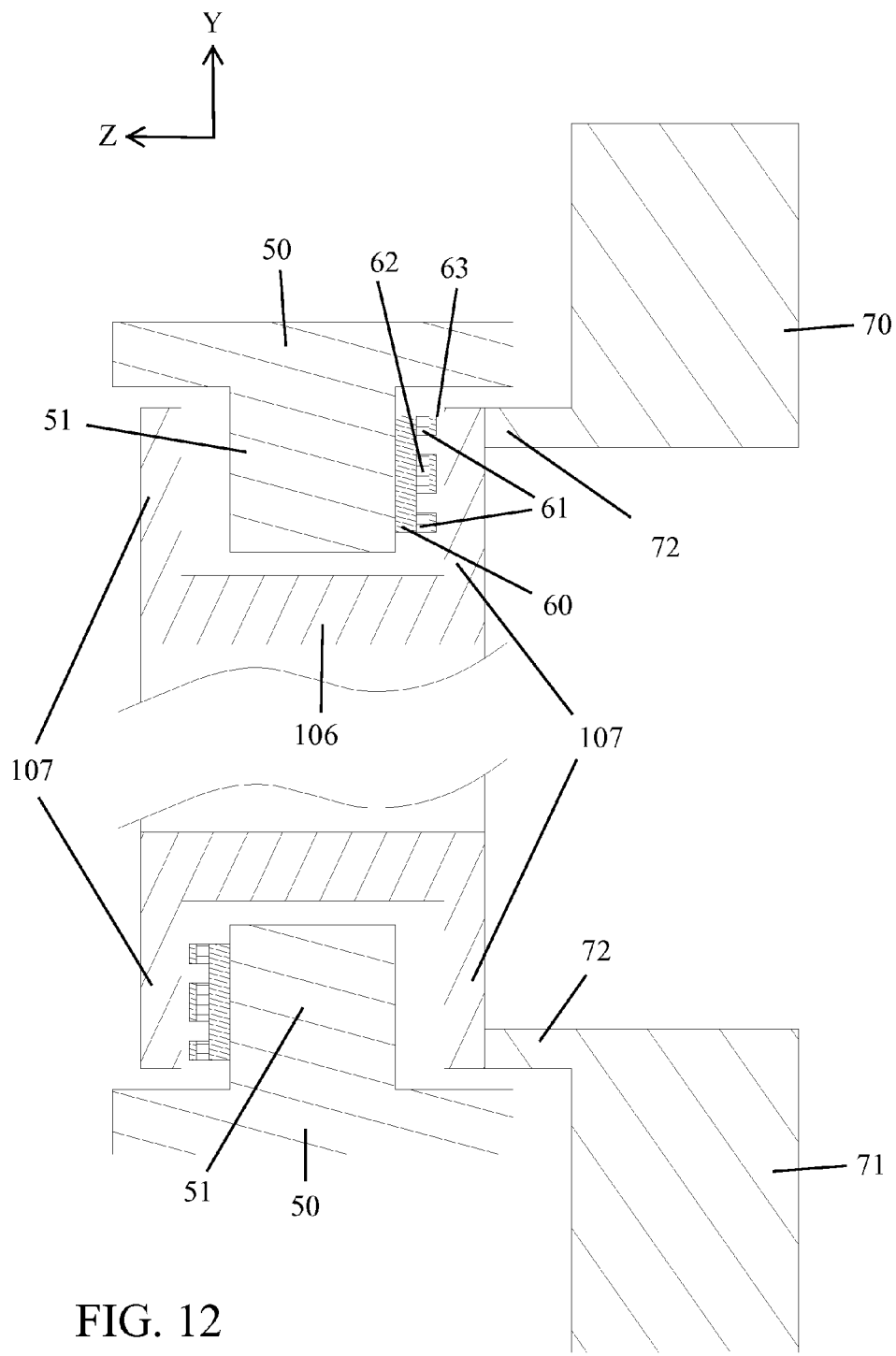
FIG. 12 shows a cross-section through a fourth representative embodiment of the present teachings.

FIG. 12 shows a further modification of the present teachings that may be advantageously utilized with any of the preceding or subsequent embodiments disclosed herein.

Similar to the embodiment shown in FIG. 11, a substantially U-shaped rotor 106 with two annular flanges 107 is again provided. The annular mounting flange 51 of the stationary housing 50 is disposed between the annular flanges 107 and is shown wider in FIG. 12 for illustrative purposes. That is, the annular mounting flange 51 may be the same width in each of the embodiments disclosed herein.

First and second drums (containers) 70, 71 are fixedly mounted on diametrically opposite sides of the rotor 106, e.g., via a bracket 72. The first drum 70 may retain, e.g., the radiation source 2 such as an X-ray tube, and the second drum 71 may retain, e.g., the radiation detector 3.

Because the first and second drums 70, 71 are mounted onto one longitudinal (axial) edge of the rotor 106, they generate a tilt or moment that acts in the rightward or clockwise direction in FIG. 12. While it is possible to use the above-described axial actuator pairs to offset this tilt (moment), it is preferable to provide a set of permanent magnets 61, 62 such that at least one permanent magnet 61, 62 is disposed on one axial (longitudinal) side of the annular mounting flange 51 and at least one permanent magnet 61, 62 is disposed on the opposite axial (longitudinal) of the annular mounting flange 51.

In addition or in the alternative, a single drum extending 360° around the axis of rotation can be fixedly mounted to the annular flange 107, within which equipment is mounted on opposite sides, in locations represented by the separate drums 70 and 71 in FIG. 12.

Each set of permanent magnets may include two S-poles 61 and one N-pole 62, or vice versa. The magnets 61, 62 are fixedly mounted onto the annular mounting flange 51 via a mounting bracket 60. Also, steel channeling plates 63 may be affixed to the axial side of the magnets 61, 62 opposite of the mounting bracket 60 to help channel the magnetic field to the adjacent annular flange 107. Again, each annular flange 107 comprises, at least in part, a magnetically-permeable material disposed on or proximal to an outer circumference of the annular rotor 106. Therefore, each set of the permanent magnets 61, 62 pulls the respective annular flange 107 towards it so as to at least partially offset the tilt or moment in the clockwise direction. In addition or in the alternative, permanent magnet assemblies with two, three (shown in FIG. 12) or four or more poles can be employed.

More specifically, the set of magnets 61, 62 shown above in FIG. 12, i.e. proximal to the drum 70, pulls the right-side annular flange 107 towards the left in FIG. 12. On the other hand, the set of magnets shown below in FIG. 12, i.e. proximal to the drum 71, pulls the left-side annular 107 towards the right in FIG. 12.

The two sets of magnets preferably pull with equal forces but in opposite directions. Therefore, no net force is applied in the axial (longitudinal direction), however a net torque or moment is applied to the rotor 106 to effectively balance or offset the moment or tilting force generated by the drums 70, 71.

By using permanent magnets 61, 62, the load on the axial actuator pairs (coils and stator cores) is reduced and thus the axial actuator pairs can be designed smaller and/or to consume less energy. Moreover, the permanent magnets 61, 62 will continue to apply a net torque or moment to the rotor 106, even when the CT machine is powered off, thereby partially maintaining the rotor 106 in the preferred upright position, and thereby minimizing or eliminating the force that could be applied to the stationary auxiliary bearing components in the axial direction in the resting state of the CT machine, or during a malfunction. Therefore, the magnetic force applied to the annular flanges 107 by the at least two sets of permanent magnets 61, 62 preferably is selected to exactly or substantially exactly equal the tilting force or moment generated by the drums 70, 71.

In FIG. 12, two sets of permanent magnets 61, 62 are shown and are disposed at an uppermost vertical position and a lowermost vertical position, respectively, relative to the rotor 106. That is, the permanent magnets 61, 62 are disposed at 12 o'clock and 6 o'clock when the rotor 106 is viewed along the Z-axis.

However, more than two sets of permanent magnets 61, 62 may be utilized to offset the tilt or moment of the drums 70, 71. For example, three sets of permanent magnets 61, 62 could be utilized, wherein one set is disposed, e.g., at an uppermost vertical position (e.g., approximately 12 o'clock) and the other two sets are disposed in a mirror-symmetric manner relative to a vertical axis (i.e. extending in the Y-direction) along a lower portion of the housing 50, such as e.g., at 5 o'clock and 7 o'clock, or at 4 o'clock and 8 o'clock. In this case, the uppermost set of permanent magnets 61, 62 is affixed to the annular mounting flange 51 on the axial side closest to the drums 70, 71 and the two lowermost sets of permanent magnets 61, 62 are affixed to the annular mounting flange 51 on the axial side farthest from the drums 70, 71.

Naturally, various other arrangements of the permanent magnetic are possible. For example, the permanent magnets 61, 62 may be disposed separate from the axial actuator pairs 24, 26 (124, 126, 127) or may be integrated with or into one or more of the axial actuator pairs. In addition or in the alternative, two or more sets of permanent magnets 61, 62 may be disposed on the axial side of the annular mounting flange 51 closest to the drums 70, 71.

Further, each of the permanent magnets 61, 62 may be comprised of a plurality of smaller magnets.

Figure 13:
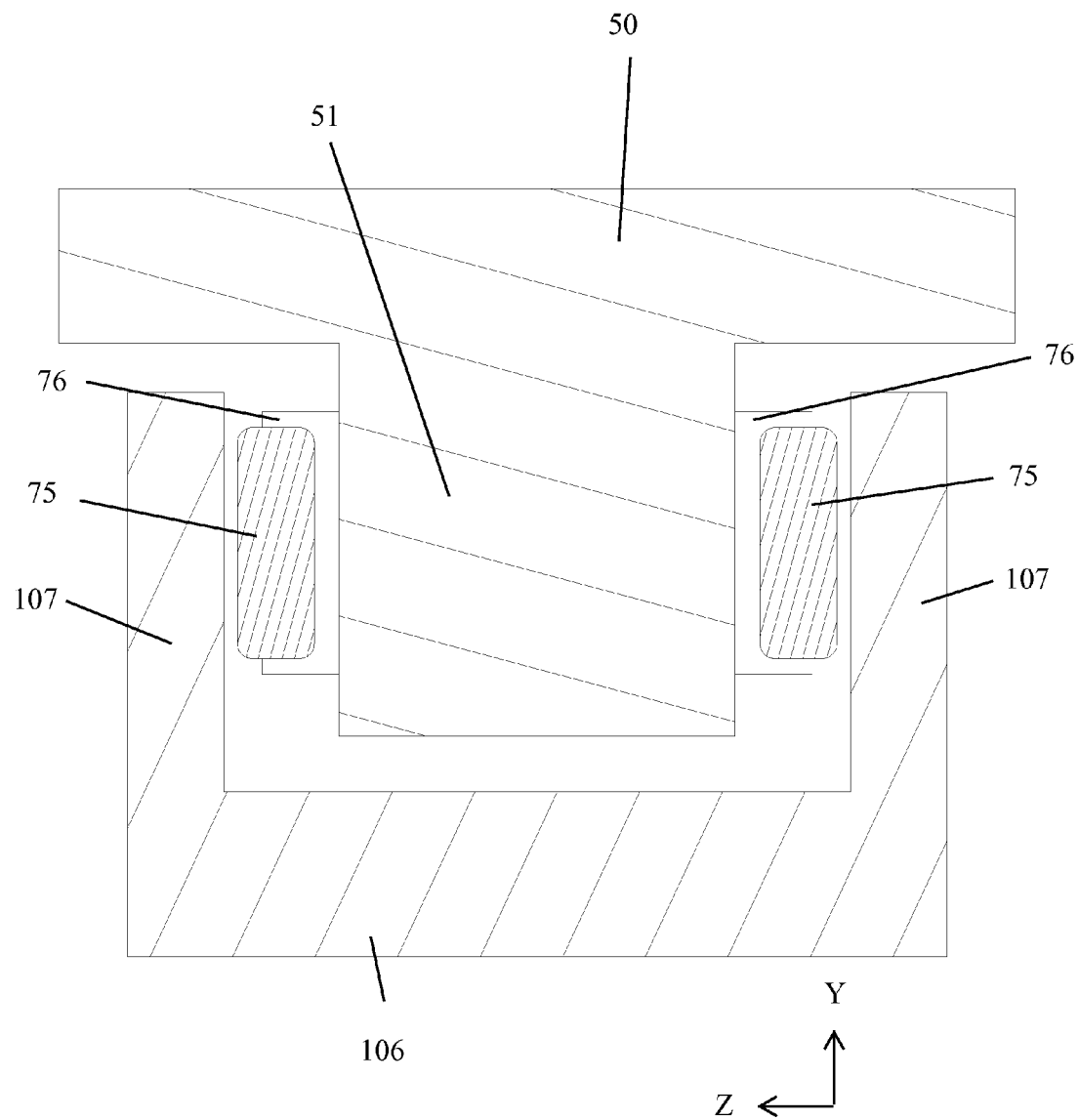
FIG. 13 shows a cross-section through a fifth representative embodiment of the present teachings.

FIG. 13 shows a further modification of the present teachings that may be advantageously utilized with any of the preceding or subsequent embodiments disclosed herein.

In FIG. 13, a pair of landing pads 75 is fixedly attached on opposite axial sides of the annular mounting flange 51 via respective landing pad holders 76. The landing pads 75 may also be referred to as plain bearings or plain bearing pads and are preferably made from an abradable graphite compound. However, other materials may be used instead of graphite.

The landing pads 75 are designed to support the rotor 106 in the axial direction in the event of a malfunction, e.g., a power loss, that would otherwise cause one of the annular flanges 107 to crash against the annular mounting flange 51 (or any of the lift actuator(s) 10, 10', the radial actuator(s) 12, 12', the axial actuators 24, 26 (124, 126, 127), position sensors 9, or any other sensitive or fragile equipment that may be disposed in the well defined by the rotor 106 and two annular flanges 107). That is, in the event that the rotor 106 drifts too far to the left or right (i.e. in the axial direction), one of the annular flanges 107 can contact the adjacent landing pad 75 without causing harm (or while minimizing harm) to the rotor assembly, the electronic equipment (e.g., actuators) or the housing 50.

Therefore, the landing pads 75 are preferably designed to have a longer length in the axial (longitudinal), i.e. along the Z-axis, than any of the other equipment (e.g., actuators) mounted on the annular mounting flange 51. In this case, the annular flange 107 will contact the adjacent landing pad 75 and thus be blocked or prevented from moving further in the axial direction, which could cause any of the sensitive or fragile equipment mounted on the annular mounting flange 51 to be crushed or otherwise damaged.

While FIG. 13 only shows one pair of landing pads 75, of course a plurality of pairs of landing pads 75 may be disposed around the circumference of the annular mounting flange 51. For example, two, three, four, five, six or more pairs of landing pads 75 may be disposed, e.g., equidistantly, around the circumference of the annular mounting flange 51. Moreover, the landing pads 75 may optionally be disposed in pairs (i.e. axially opposite of each other) or may be offset from each other in the circumferential direction of the rotor 106 and/or flange(s) 107

Additional, non-limiting aspects of the present teachings are as follows:

1. An apparatus comprising:
   an annular rotor configured to be rotated about a rotational axis, the rotor having (i) a hollow interior sized to receive a patient, (ii) a longitudinal length less than its diameter and (iii) a magnetically-permeable material disposed on or proximal to an outer circumference of the rotor,
   a radiation source affixed to the rotor so as to rotate therewith,
   at least one optional non-magnetic bearing disposed around the outer circumference of the rotor, and
   a magnetic bearing system configured to influence the position of the rotor in three-dimensional space and preferably including at least three actuators configured to generate a magnetic field that interacts with the magnetically-permeable material of the rotor, wherein:
   at least one optional lift actuator generates a force for lifting the rotor in a vertical direction,
   at least one optional radial actuator influences the position of the rotor in the radial direction of the rotor and at least assists in maintaining an annular gap between the rotor and the at least one optional non-magnetic bearing in a radial direction of the rotor while the rotor is rotating under control of the magnetic bearing system, and
   at least one axial actuator influences the position of the rotor in an axial direction of the rotor, e.g., by maintaining an annular gap (e.g., a predetermined annular gap) between the rotor (and/or at least one radially-extending flange thereof) and the at least one optional non-magnetic bearing (e.g., axial landing pad) in the axial direction of the rotor while the rotor is rotating under control of the magnetic bearing system.
2. An apparatus as in aspect 1, wherein the rotor includes at least one annular flange comprising, at least in part, a magnetically-permeable material, the at least one axial actuator being disposed proximal to the annular flange.
3. An apparatus as in aspect 2, wherein the at least one axial actuator comprises a pair of axial actuators, each configured to generate a variable magnetic field independent of the other, the annular flange optionally being disposed within a radially-extending gap defined between the pair of axial actuators.
4. An apparatus as in any one of aspects 1-3, wherein the apparatus comprises at least three axial actuators fixedly disposed around the rotor and being spaced approximately equidistantly to each other.
5. An apparatus as in any one of aspects 1-4, wherein the at least one lift actuator comprises at least one permanent magnet configured to lift at least 50% of the weight of the rotor.
6. An apparatus as in any one of aspects 1-5, wherein the at least one lift actuator comprises an electromagnet configured to generate a variable magnetic field.
7. An apparatus as in any one of aspects 1-6, wherein:
   the rotational axis extends substantially in a horizontal direction.
8. An apparatus as in any one of aspects 1-7, wherein:
   the at least one non-magnetic bearing is selected from a plain bearing and a rolling-element bearing.
9. An apparatus comprising:
   an annular rotor having at least one annular flange and comprising, at least in part, a magnetically-permeable material disposed on or proximal to an outer circumference of the annular rotor and the annular flange, the rotor being rotatable about a rotational axis,
   at least one optional non-magnetic bearing disposed adjacent to the annular rotor and capable of rotatably supporting the annular rotor at least temporarily, wherein the outer circumference of the annular rotor has a diameter slightly less than the diameter of a radially-inward-facing surface of the non-magnetic bearing and
   a magnetic bearing system disposed adjacent to the outer circumference of the annular rotor, the magnetic bearing system comprising:
   at least one optional lift actuator generating a magnetic field and being fixedly disposed adjacent to a vertically upper portion of the annular rotor, the at least one lift actuator being configured to generate a force that lifts the annular rotor in a vertical direction at least while the annular rotor is rotating about the rotational axis,
   at least one optional radial actuator generating a variable magnetic field and being fixedly disposed adjacent to the outer circumference of the annular rotor, the at least one radial actuator being configured to influence the position of the annular rotor in the radial direction of the annular rotor while the annular rotor is rotating so as to maintain an annular clearance between the radially-inward-facing surface of the at least one non-magnetic bearing and the outer circumference of annular rotor, and
   at least one axial actuator generating a variable magnetic field and being fixedly disposed adjacent to the at least one annular flange, the at least one axial actuator being configured to influence the position of the annular rotor in an axial direction of the rotor, preferably to maintain a predetermined annular gap between the annular rotor and/or the at least one annular flange and an axially-adjacent, optional non-magnetic bearing, e.g., one or more axial landing pads.
10. An apparatus as in aspect 9, wherein the at least one axial actuator comprises a pair of axial actuators, each configured to generate a variable magnetic field independent of the other, the annular flange optionally being disposed within a radially-extending gap defined between the pair of axial actuators.

11. An apparatus as in aspect 9 or 10, wherein the apparatus comprises at least three axial actuators fixedly disposed around the rotor and being spaced approximately equidistantly to each other.

12. An apparatus as in any one of aspects 9-11, wherein the rotational axis extends substantially in a horizontal direction.

13. An apparatus as in any one of aspects 9-12, wherein the at least one lift actuator comprises at least one permanent magnet configured to lift at least 50% of the weight of the annular rotor.

14. An apparatus as in any one of aspects 9-13, wherein the at least one lift actuator further comprises an electromagnet configured to generate a variable magnetic field.

15. An apparatus as in any one of aspects 9-14, wherein the apparatus comprises at least three radial actuators disposed around the outer circumference of the annular rotor.

16. An apparatus as in any one of aspects 9-15, wherein the at least one non-magnetic bearing is selected from a plain bearing and a rolling-element bearing.

17. An apparatus as in any one of aspects 9-17, wherein the rotor has an outer diameter that is greater than its longitudinal length.

18. An apparatus as in any one of aspects 9-17, wherein the rotor has a hollow interior sized to receive a patient therein.

19. An apparatus as in any one of aspects 9-18, wherein the apparatus is a diagnostic scanning apparatus and further comprises a radiation source mounted on the annular rotor so as to rotate therewith.

20. An apparatus as in aspect 19, wherein:
the rotational axis extends substantially in a horizontal direction,
the at least one lift actuator comprises at least one permanent magnet configured to lift at least 50% of the weight of the annular rotor and an electromagnet configured to generate a variable magnetic field,
the at least one non-magnetic bearing is selected from a plain bearing and a rolling-element bearing, and
wherein the apparatus comprises:
at least three axial actuators fixedly disposed around the annular rotor, the annular flange being disposed within respective spacings defined in each of the axial actuators and
at least three radial actuators disposed around the outer circumference of the rotor.

21. An apparatus as in any one of aspects 9-20, further comprising a radiation detector mounted on the annular rotor generally opposite of the radiation source.

22. An apparatus comprising:
an annular rotor having at least one annular flange extending in a radial direction of the annular rotor, the annular rotor comprising, at least in part, a magnetically-permeable material on or adjacent to at least one circumferential surface and the annular rotor being rotatable about a rotational axis,
at least one optional non-magnetic bearing disposed adjacent an outer circumference of the annular rotor,
at least one optional radial actuator disposed adjacent to the outer circumferential portion of the annular rotor, the at least one radial actuator being controllable to influence the position of the annular rotor in a plane perpendicular to rotational axis while the annular rotor rotates so as to maintain an annular gap between the at least one non-magnetic bearing and the annular rotor, and
at least three axial actuators disposed around the circumference of the annular rotor in a spaced relationship relative to each other, the at least one annular flange optionally being disposed within a spacing defined in each of the axial actuators, each axial actuator comprising an electromagnet that is controllable to influence the position of the at least one annular rotor in an axial direction of the annular rotor, preferably to maintain a predetermined annular gap between the annular rotor and/or the at least one annular flange and an axially-adjacent, optional non-magnetic bearing, e.g., one or more axial landing pads.

23. An apparatus as in aspect 22, wherein the apparatus comprises at least three radial actuators disposed adjacent to the outer circumferential portion of the annular rotor in a spaced relationship relative to each other, wherein at least one of the radial actuators comprises at least one permanent magnet configured to vertically lift at least 50% of the weight of the annular rotor.

24. An apparatus as in aspect 22 or 23, wherein the annular rotor has an outer diameter that is greater than its longitudinal length.

25. An apparatus as in any one of aspects 22-24, wherein the apparatus is a diagnostic scanning apparatus and further comprises a radiation source mounted on the annular rotor so as to rotate therewith.

26. An apparatus as in any one of aspects 1-25, wherein at least one of the actuators comprises a laminated core.

27. An apparatus as in any one of aspects 1-26, wherein first and second (e.g., annular) flanges extend radially outward from the rotor preferably in a parallel, spaced-apart relationship, each of the first and second flanges comprising, at least in part, a magnetically-permeable material.

28. An apparatus as in aspect 27, wherein the first flange is formed integrally with the rotor without a seam therebetween and the second flange is detachably attached to the rotor.

29. An apparatus as in aspect 27 or 28, wherein the rotor and the flanges form a rotor assembly having at least substantially a U-shape in cross-section.

30. An apparatus as in any one of aspects 27-29, wherein a well is defined by adjacent surfaces of the rotor and flanges.

31. An apparatus as in aspect 30, wherein first and second axial actuators are disposed within the well, the first axial actuator being configured to act on the first flange and the second axial actuator being configured to act on the second flange.

32. An apparatus as in aspect 31, wherein the first and second axial actuator each comprise at least one coil wound around at least one stator core.

33. An apparatus as in aspect 30 or 31, wherein the first and second axial actuator each comprise a substantially U-shaped stator core and two coils respectively wound around the two legs of the stator core.

34. An apparatus as in any one of aspects 31-33, further comprising a stationary housing or frame having an (e.g., annular) mounting flange extending radially inward from the stationary housing or frame into the space between the first and second annular flanges, wherein the first and second axial actuators are affixed to the mounting flange.

35. An apparatus as in any one of aspects 1-34, further comprising:
a (the) stationary housing or frame having an (the) mounting flange extending radially inward from the stationary housing or frame into the space between (the) first and second flanges that extend from the rotor preferably in a parallel, spaced-apart relationship and that each comprise, at least in part, a magnetically-permeable material,
at least one first permanent magnet affixed to the mounting flange on the axial side closest to one or more drums affixed to the rotor and containing a radiation source and/or a radiation detector, the at least one first permanent magnet being proximal to the first flange, and at least one second permanent magnet affixed to the mounting flange on the axial side farthest from the one or more drums affixed to the rotor and containing the radiation source and/or the radiation detector, the at least one second permanent magnet being proximal to the second flange.

36. An apparatus as in aspect 35, wherein the at least one first permanent magnet and the at least one second permanent magnet apply no net force to the rotor in the axial direction, but apply a net torque or moment to the rotor that balances or offsets a tilting force (load) or moment caused by the weight of the drum(s).

37. An apparatus as in aspect 35 or 36, wherein the at least one first permanent magnet is disposed higher in the vertical direction that the at least one second permanent magnet.

38. An apparatus as in any one of aspects 35-37, wherein at least one first permanent magnet is disposed generally at an uppermost vertical position of the mounting flange and the at least one second permanent magnet is disposed generally at a lowermost vertical position of the mounting flange.

39. An apparatus as in any one of aspects 35-38, wherein at least one first permanent magnet and/or the at least one second permanent magnet is comprised of at least two separate and distinct permanent magnets that are spaced apart in a mirror-symmetric manner relative to a vertical axis of the rotor.

40. An apparatus as in any one of aspects 35-39, further comprising at least one steel channeling member or plate affixed to each permanent magnet.

41. An apparatus as in any one of aspects 1-40, further comprising:

a (the) stationary housing or frame having an (the) mounting flange extending radially inward from the stationary housing or frame into the space between (the) first and second flanges that extend from the rotor preferably in a parallel, spaced-apart relationship, at least one first landing pad affixed to the mounting flange on one axial side so as to be proximal to the first flange, and at least one second landing pad affixed to the mounting flange on the opposite axial side so as to be proximal to the second flange.

42. An apparatus as in aspect 41, wherein the at least one first landing pad and/or the at least one second landing pad is a plain bearing or plain bearing pad.

43. An apparatus as in aspect 41 or 42, wherein the at least one first landing pad and/or the at least one second landing pad comprises an abradable material, such as an abradable graphite material.

44. An apparatus as in any one of aspects 41-43, wherein the at least one first landing pad and/or the at least one second landing pad have an outer axial surface that is spaced farther from the mounting flange than any other equipment affixed to the mounting flange.

45. An apparatus as in any one of aspects 41-44, further comprising two or more first landing pads and/or two or more second landing pads, each being disposed, e.g., equidistantly around the circumference of the mounting flange.

REFERENCE NUMBER LIST 1, 1' Computed tomography machine
2 Radiation source
3 Radiation detector
4 Hollow interior of rotor 6
5 Annular gap
6 Rotor (annular gantry)
7 Annular flange
8 Rotational axis of rotor 6
8' Ideal rotational axis of rotor 6
9 Position sensor
10, 10' Lift actuator
11 Outer circumference of rotor 6
12, 12' Radial actuator
14 Axial actuator
16 Stator core
18 Permanent magnet
20 Stator core
22 Coil
24 Stator core
25 Spacing
26 Coil
28 Auxiliary bearing
30 Coil
32 Stator core
34 Coil
40 Ring shaft
41 Curved bearing
42 Curved tubular housing
43 Inner surface
44 Annular connecting flange
46 Bearing cage
48 Annular clearance
50 Stationary housing
51 Annular mounting flange
60 Mounting bracket
61 N-pole of magnet
62 S-pole of magnet
63 Steel channeling member
70 Drum
71 Drum
72 Bracket
75 Landing pad
76 Landing pad holder
106 Rotor
107 Annular flange
124 Stator core
126 Coil
127 Coil

The invention claimed is:

1. An apparatus comprising:

a rotor that is rotatable about a rotational axis, has a hollow interior and comprises, at least in part, a magnetically-permeable material, first and second flanges connected to and extending radially outward from the rotor in a spaced-apart relationship, each of the first and second flanges comprising, at least in part, a magnetically-permeable material, a first axial actuator configured to generate a variable magnetic field, the first axial actuator being fixedly disposed adjacent to, but spaced from, the first flange and configured to magnetically pull the first flange in a first axial direction of the rotor, and a second axial actuator configured to generate a variable magnetic field, the second axial actuator being fixedly disposed adjacent to, but spaced from, the second flange and configured to magnetically pull the second flange in a second axial direction of the rotor that is opposite of the first axial direction, wherein the first and second axial actuators are both at least substantially disposed between the first and second flanges.

2. The apparatus as in claim 1, wherein the first flange is formed integrally with the rotor without a seam therebetween and the second flange is detachably attached to the rotor.

3. The apparatus as in claim 1, wherein:
the first and second flanges are annular shaped,
the first and second annular flanges extend at least substantially in parallel to each other, and
the rotor, the first annular flange and the second annular flange together form a rotor assembly having at least substantially a U-shape in cross-section.

4. The apparatus as in claim 3, further comprising:
a stationary housing having a mounting flange extending radially inward from the stationary housing into a hollow space between the first and second flanges,
wherein the first axial actuator is affixed to a first axial side of the mounting flange that is closest to the first flange, and
the second axial actuator is affixed to a second axial side of the mounting flange that is closest to the second flange, the second axial side being opposite of the first axial side.

5. The apparatus as in claim 4, wherein the apparatus comprises:
at least three first axial actuators affixed to the first axial side of the mounting flange and being spaced approximately equidistantly to each other around a circumference of the mounting flange; and
at least three second axial actuators affixed to the second axial side of the mounting flange and being spaced approximately equidistantly to each other around the circumference of the mounting flange.

6. The apparatus as in claim 4, further comprising:
at least one bracket affixed to the rotor and/or to first flange and extending axially outward of the rotor and the first flange,
at least one first permanent magnet affixed to the first axial side of the mounting flange and proximal to, but spaced from, the first flange, and
at least one second permanent magnet affixed to the second axial side of the mounting flange and proximal to, but spaced from, the second flange.

7. The apparatus as in claim 6, wherein the at least one bracket is attached to a radiation source or to a radiation detector.

8. The apparatus as in claim 6, wherein the at least one first permanent magnet and the at least one second permanent magnet together apply no net force to the rotor in the axial direction, but apply a net torque or moment to the rotor that balances or offsets a tilting force caused by the weight of the bracket and any equipment attached to the bracket that is disposed axially outward of the rotor and first flange.

9. The apparatus as in claim 8, wherein the at least one first permanent magnet is disposed higher in a vertical direction of the stationary housing than the at least one second permanent magnet.

10. The apparatus as in claim 9, further comprising at least one steel channeling member affixed to each of at least one permanent magnet.

11. The apparatus as in claim 4, further comprising:
at least one first landing pad affixed to the first axial side of the mounting flange so as to be proximal to the first flange, and
at least one second landing pad affixed to the second axial side of the mounting flange so as to be proximal to the second flange.

12. The apparatus as in claim 11, wherein the at least one first landing pad and/or the at least one second landing pad is a plain bearing or plain bearing pad.

13. The apparatus as in claim 12, wherein the at least one first landing pad and/or the at least one second landing pad comprises an abradable graphite material.

14. The apparatus as in claim 11, wherein the at least one first landing pad and/or the at least one second landing pad have an outer axial surface that is spaced farther from the mounting flange than any other equipment affixed to the mounting flange.

15. The apparatus as in claim 14, further comprising:
at least one bracket affixed to the rotor and/or to first flange and extending axially outward of the rotor and the first flange,
a radiation source or a radiation detector affixed to the at least one bracket axially outward of the first flange,
at least one first permanent magnet affixed to the first axial side of the mounting flange and proximal to, but spaced from, the first flange,
at least one second permanent magnet affixed to the second axial side of the mounting flange and proximal to, but spaced from, the second flange, the at least one second permanent magnet being disposed lower in a vertical direction of the stationary housing than the at least one first permanent magnet,
a first steel channeling plate affixed to the at least one first permanent magnet so as to be disposed between the at least one first permanent magnet and the first flange, and
a second steel channeling plate affixed to the at least one second permanent magnet so as to be disposed between the at least one second permanent magnet and the second flange,
wherein:
the at least one first permanent magnet and the at least one second permanent magnet together apply no net force to the rotor in the axial direction, but apply a net torque or moment to the rotor that balances or offsets a tilting force caused by the weight of the bracket and any equipment attached to the bracket that is disposed axially outward of the rotor and first flange, and
the at least one first landing pad and/or the at least one second landing pad is a plain bearing or plain bearing pad comprised of an abradable graphite material.

16. A method of scanning, imaging or treating a patient or an object comprising:
rotating the rotor of the apparatus of claim 7 and
actuating the rotating radiation source attached to the bracket to irradiate the patient or the object.

17. The apparatus as in claim 1, wherein the first flange has an inner surface and an exposed outer surface and the second flange has an inner surface and an exposed outer surface, wherein the inner surface of the second flange faces the inner surface of the first flange, wherein the first axial actuator faces the inner surface of the first flange and the second axial actuator faces the inner surface of the second flange and wherein no additional axial actuators face the exposed outer surface of the first flange or the exposed outer surface of the second flange.

18. The apparatus as in claim 1, wherein each of the first and second flanges comprise: an outer diameter, an axial thickness and a radial length greater than the axial thickness and wherein the outer diameter of the first flange is substantially equal to the outer diameter of the second flange.

19. The apparatus as in claim 1, wherein the rotor includes a cylindrical outer surface facing radially away from the rotation axis, wherein the first flange includes a first end and a second end, wherein the first end of the first flange is at a first location on the cylindrical outer surface and the second end of the first flange is radially spaced from the first end of the first flange and wherein the second flange has a first end and a second end, wherein the first end of the second flange is at a second location on the cylindrical outer surface, the second location being axially spaced from the first location, and the second end of the second flange is radially spaced from the first end of the second flange and axially spaced from the second end of the first flange.

20. The apparatus as in claim 4, wherein the first flange has an inner surface and an exposed outer surface, the second flange has an inner surface and an exposed outer surface, the inner surface of the second flange facing the inner surface of the first flange, wherein the first axial actuator faces the inner surface of the first flange and the second axial actuator faces the inner surface of the second flange and wherein no additional axial actuators face the exposed outer surface of the first flange or the exposed outer surface of the second flange.

* * * * *